US010393658B2

(12) United States Patent
Dehe et al.

(10) Patent No.: US 10,393,658 B2
(45) Date of Patent: Aug. 27, 2019

(54) GAS ANALYSIS APPARATUS

(71) Applicant: Infineon Technologies AG, Neubiberg (DE)

(72) Inventors: Alfons Dehe, Villingen Schwenningen (DE); Christoph Glacer, Munich (DE); David Tumpold, Kirchheim (DE)

(73) Assignee: Infineon Technologies AG, Neubiberg (DE)

( * ) Notice: Subject to any disclaimer, the term of this patent is extended or adjusted under 35 U.S.C. 154(b) by 0 days.

(21) Appl. No.: 15/854,848

(22) Filed: Dec. 27, 2017

(65) Prior Publication Data

US 2018/0188172 A1    Jul. 5, 2018

(30) Foreign Application Priority Data

Dec. 29, 2016  (DE) .................. 10 2016 125 840

(51) Int. Cl.
*G01N 21/63* (2006.01)
*G01N 21/17* (2006.01)

(52) U.S. Cl.
CPC ......... *G01N 21/63* (2013.01); *G01N 21/1702* (2013.01); *G01N 2021/1704* (2013.01)

(58) Field of Classification Search
CPC .............. G01N 21/63; G01N 21/1702; G01N 2021/1704
See application file for complete search history.

(56) References Cited

U.S. PATENT DOCUMENTS

| 4,393,311 | A | * | 7/1983 | Feldman | ................. | C23F 4/00 |
| | | | | | | 250/459.1 |
| 5,220,173 | A | * | 6/1993 | Kanstad | ................. | B41J 2/32 |
| | | | | | | 250/493.1 |
| 2006/0139646 | A1 | | 6/2006 | DiFoggio | | |
| 2009/0039267 | A1 | * | 2/2009 | Arndt | ............. | G01N 21/3504 |
| | | | | | | 250/353 |
| 2010/0118301 | A1 | * | 5/2010 | Vondras | ................. | G01J 3/10 |
| | | | | | | 356/318 |
| 2013/0265770 | A1 | * | 10/2013 | Breidenassel | ........... | F21V 7/00 |
| | | | | | | 362/296.01 |
| 2015/0101395 | A1 | * | 4/2015 | Dehe | ............... | G01N 29/2418 |
| | | | | | | 73/24.02 |
| 2015/0192517 | A1 | | 7/2015 | Andre | | |

(Continued)

FOREIGN PATENT DOCUMENTS

DE     102016205024 A1    9/2016

*Primary Examiner* — Hina F Ayub
(74) *Attorney, Agent, or Firm* — Viering, Jentschura & Partner MBB

(57) ABSTRACT

An analysis apparatus includes a gas chamber for receiving a gas to be analyzed, a source to emit radiation into the chamber. The radiation is to selectively excite molecules of the gas. The apparatus further includes a sensor to detect a physical variable which contains information about a degree of interaction between the radiation and the gas. The source includes a heatable planar radiation element to emit radiation and a housing with a first wall and a second wall which, therebetween, define and immediately delimit a radiation element receptacle chamber that is separated in a fluid-tight manner from the surroundings of the source. At least one of the first or second housing wall is transparent to the electromagnetic radiation that is emittable by the radiation element.

26 Claims, 24 Drawing Sheets

(56) References Cited

U.S. PATENT DOCUMENTS

2015/0233557 A1\* 8/2015 Aoyama .............. F21V 21/145
362/183
2015/0316472 A1 11/2015 Yon et al.
2016/0282259 A1 9/2016 Kolb et al.

\* cited by examiner

GAS ANALYSIS APPARATUS

CROSS-REFERENCE TO RELATED APPLICATION

This application claims priority to German Patent Application Serial No. 10 2016 125 840.7, which was filed Dec. 29, 2016, and is incorporated herein by reference in its entirety.

TECHNICAL FIELD

Various embodiments relate generally to a gas analysis apparatus.

BACKGROUND

Gas analysis apparatuses have become very important in the recent past, which, inter alia, can be ascribed to the necessity of a precise determination of the composition of the ambient air. This necessity is due to, in particular, increasing environmental pollution.

Gas analysis apparatuses may be configured to excite, by means of electromagnetic radiation, gas molecules of a gas to be analysed and ascertain, by means of a sensor, the degree of interaction between the electromagnetic radiation and the respective gas molecules. Here, it is possible, in general, to selectively excite the molecules of a gas whose concentration is to be ascertained such that the degree of interaction, which is ascertainable by means of the sensor, represents a measure for the concentration of the gas to be analysed.

In order to be able to ensure a selective excitation of gas molecules of a gas to be analysed, it is necessary to ensure well-defined low thermal coupling between a radiation source, which is configured to emit the electromagnetic radiation, and the gas to be analysed in order not to inadvertently excite gas molecules of other gases, which would falsify the measurement.

SUMMARY

An analysis apparatus includes a gas chamber for receiving a gas to be analysed, a source to emit radiation into the chamber. The radiation is to selectively excite molecules of the gas. The apparatus further includes a sensor to detect a physical variable which contains information about a degree of interaction between the radiation and the gas. The source includes a heatable planar radiation element to emit radiation and a housing with a first wall and a second wall which, therebetween, define and immediately delimit a radiation element receptacle chamber that is separated in a fluid-tight manner from the surroundings of the source. At least one of the first or second housing wall is transparent to the electromagnetic radiation that is emittable by the radiation element.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which.

DESCRIPTION

The following detailed description refers to the accompanying drawings that show, by way of illustration, specific details and embodiments in which the invention may be practiced.

The word "exemplary" is used herein to mean "serving as an example, instance, or illustration". Any embodiment or design described herein as "exemplary" is not necessarily to be construed as preferred or advantageous over other embodiments or designs.

By way of "planar", the present application denotes the geometry of a component which has a substantially greater extent in a first direction and in a second direction that is orthogonal to the first direction than in a third direction, corresponding to a thickness direction, that is orthogonal to the first direction and the second direction.

Figure 1:
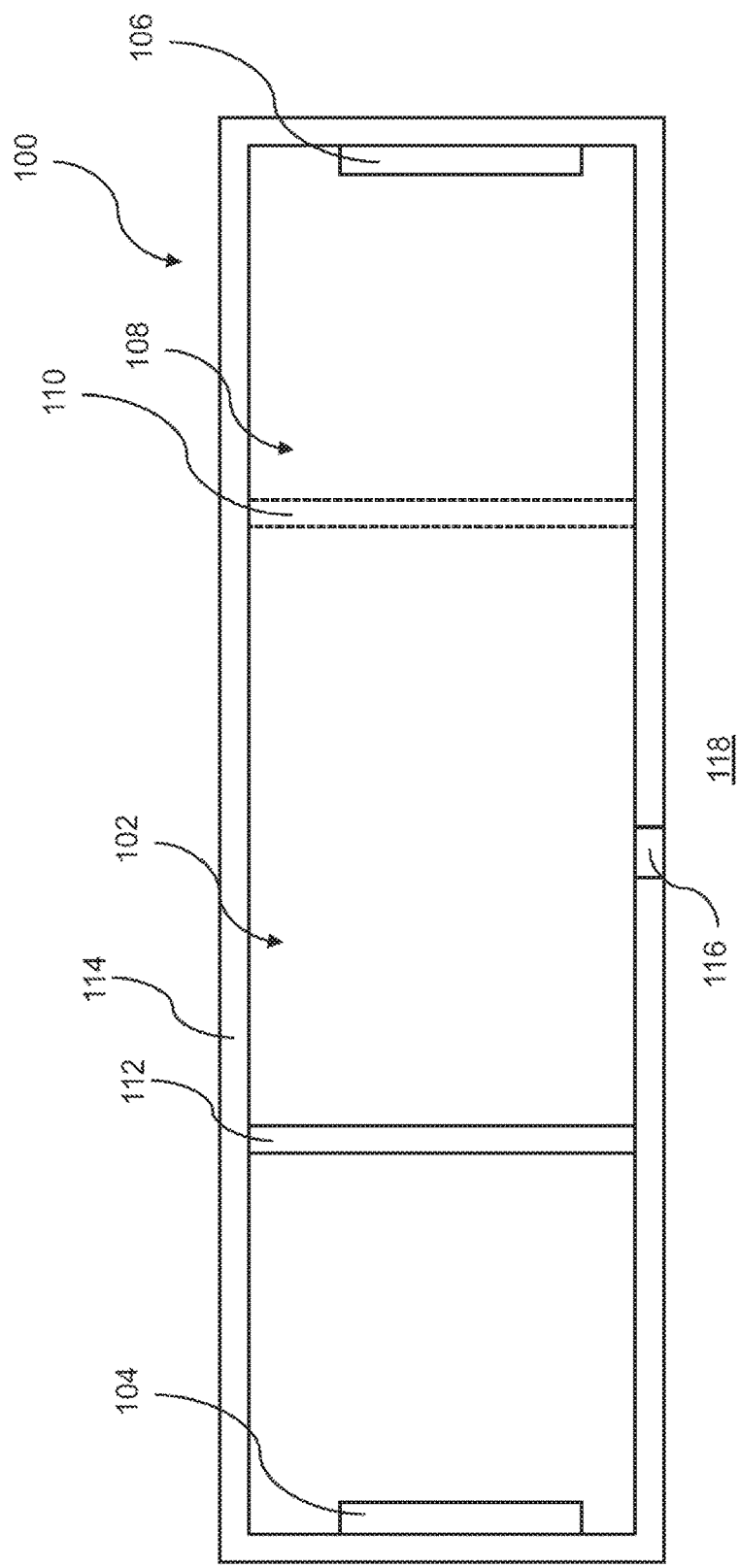
FIG. 1 shows a schematic illustration of a gas analysis apparatus.

FIG. 1 is a schematic view of an exemplary gas analysis apparatus 100. The gas analysis apparatus 100 has: a gas chamber 102 which is configured to receive a gas to be analysed, a radiation source 104 configured to emit electromagnetic radiation into the gas chamber 102, wherein the electromagnetic radiation is configured to selectively excite, in the gas chamber 102, gas molecules of a gas to be analysed, and a sensor 106 configured to detect a physical variable which contains information about the degree of interaction between the electromagnetic radiation that is emittable by the radiation source 104 and the gas molecules of the gas to be analysed, wherein the degree of interaction is a measure for the concentration of the gas to be analysed. By way of example, the gas can be ambient air.

The gas analysis apparatus 100 may be embodied as a photo-acoustic gas analysis apparatus. In such a gas analysis apparatus 100, the physical variable, which contains information about the degree of interaction between the electromagnetic radiation that is emittable by the radiation source 104 and the gas molecules of the gas to be analysed, corresponds to sound waves which are produced as a consequence of the interaction between the electromagnetic radiation that is emittable by the radiation source 104 and the gas molecules of the gas to be analysed. The functionality of a photo-acoustic gas analysis apparatus will be explained briefly below.

In a photo-acoustic gas analysis apparatus, the radiation source 104 is configured to emit electromagnetic radiation with a time-varying intensity, for example with a periodically time-varying intensity, into the gas chamber 102. The electromagnetic radiation that is emittable by the radiation source 104 may be configured to induce atomic and/or molecular transitions in the gas molecules of a gas to be analysed in the gas chamber 102 and/or it may be configured to excite numerous vibration modes and/or rotational modes of the gas molecules. Heat is produced during the subsequent de-excitation of the gas molecules excited in this manner, said heat leading to a local expansion of the gas received in the gas chamber 102, producing a positive pressure pulse.

The heat produced in this manner is subsequently dissipated to a thermal bath, leading to a contraction of the gas received in the gas chamber 102 and producing a negative pressure pulse. By way of example, the thermal bath may be provided by a holder that has physical contact with the photo-acoustic gas analysis apparatus 100.

Since the electromagnetic radiation is emitted into the gas chamber 102 with a time-varying intensity, the gas molecules of the gas to be analysed are excited in a time-varying manner, for example periodically. In this way, time-varying, e.g. periodic, pressure variations, i.e. sound waves, are produced in the gas received in the gas chamber 102. In such a gas analysis apparatus 100, the sensor 106 may have a sound wave sensor or may be embodied as a sound wave sensor, which is configured to detect the sound waves produced as a consequence of the interaction between the electromagnetic radiation emitted by the radiation source 104 and the gas molecules of the gas to be analysed.

The sound wave sensor 106 may be arranged within the gas chamber 102. In such a photo-acoustic gas analysis apparatus 100, the sensor response, i.e. the signal amplitude, of the sound wave sensor 106 increases with increasing concentration of the gas to be analysed. In general, such a detection scheme is referred to as direct detection scheme.

Alternatively, the photo-acoustic gas analysis apparatus 100 may be configured to capture the concentration of the gas to be analysed in a differential manner. In such a photo-acoustic gas analysis apparatus 100, the sound wave sensor 106 is not arranged in the gas chamber 102 but arranged in a reference gas chamber 108 which is sealed from the gas chamber 102 in a fluid-tight manner by a window 110 which transmits electromagnetic radiation that is emittable by the radiation source 104. A gas with a well-defined gas composition is received in the reference gas chamber 108, said gas composition containing, with a well-defined concentration, the gas type or gas variety to be analysed.

In a differential-type photo-acoustic gas analysis apparatus 100, electromagnetic radiation emitted by the radiation source 104 reaches the gas chamber 102, in which it selectively excites gas molecules of the gas to be excited, as a result of which the intensity of the electromagnetic radiation is attenuated depending on the concentration of the gas to be analysed in the gas chamber 102. The higher the concentration of the gas to be analysed in the gas chamber 102, the greater the attenuation of the intensity of the electromagnetic radiation emitted by the radiation source 104. Subsequently, the electromagnetic radiation reaches into the reference gas chamber 108 through the window 110 and once again excites gas molecules of the gas or of the gas type, the concentration of which is to be ascertained in the gas chamber 102. Since the intensity of the electromagnetic radiation penetrating into the reference gas chamber 108 reduces with increasing concentration of the gas to be analysed in the gas chamber 102, the response of the sound wave sensor 106 reduces with increasing concentration of the gas to be analysed in the gas chamber 102.

The radiation source 104 may be embodied as a blackbody emitter. A blackbody emitter emits electromagnetic radiation according to Planck's radiation law. This means that the emission spectrum thereof only depends on its temperature but not on its form or composition. During operation, the radiation source 104, or one of its components, can be heated to temperatures of more than 450° C.

The radiation source 104 may be configured to emit electromagnetic radiation in a broad wavelength range, for example in the infrared, visible and ultraviolet wavelength ranges. Infrared electromagnetic radiation with a wavelength in a range from approximately 4.170 µm to approximately 4.370 µm and from approximately 14 µm to approximately 16 µm is suitable, for example, to produce vibration modes of $CO_2$.

The sensor 106 may have a capacitive sound wave sensor or it may be embodied as such, said capacitive sound wave sensor having two spaced apart membranes which form a capacitor. One of the membranes is rigid and the other is displaceable by sound waves to be detected. A displacement of the displaceable membrane induced by sound waves to be detected may induce a change in capacitance of the capacitor, which can be read by a suitable readout circuit. The change in capacitance reflects the properties of the sound waves to be detected, for example the sound pressure.

Alternatively, or additionally, the sensor 106 may have a piezoelectric sound wave sensor or it may be embodied as such, said piezoelectric sound wave sensor having a piezoelectric layer that is deformable by sound waves to be detected. A deformation of the piezoelectric layer induces an electrical voltage therein, said electrical voltage reflecting properties of the sound waves to be detected, for example the sound pressure. The induced electrical voltage can be read by a suitable readout circuit.

Alternatively, the gas analysis apparatus 100 may be embodied as a non-dispersive radiation detector, in particular as a non-dispersive infrared (NDIR) detector or it may include the latter. In such a gas analysis apparatus 100, the sensor 106 is embodied as an optical sensor, for example as an infrared sensor, and the physical variable, which contains information about the degree of interaction between the electromagnetic radiation emitted by the radiation source 104 and the gas molecules of the gas to be analysed, is the intensity of the electromagnetic radiation detected by the radiation detector 106. The higher the concentration of the gas to be analysed in the gas chamber 102, the greater the attenuation of the intensity of the electromagnetic radiation in the gas chamber 102 and the lower the response of the sensor 106.

Moreover, the gas analysis apparatus 100 may have a window 112 which transmits electromagnetic radiation that is emittable by the radiation source 104 and which is arranged between the radiation source 104 and the gas chamber 102.

The window 112 may be embodied as a filter which is configured to transmit only a restricted wavelength range of the spectrum that is emittable by the radiation source 104, said restricted wavelength range containing at least an excitation wavelength of the gas molecules of the gas to be analysed. This renders it possible to ensure that, at a given time during the operation of the gas analysis apparatus 100, gas molecules of only one gas to be analysed are excited. This allows a high measurement accuracy to be ensured. As will be described below, the radiation source 104 may, alternatively or additionally, have a filter.

If only the concentration of a single gas is intended to be ascertained, it is possible to use a filter 112 with fixedly predetermined transmission properties. By contrast, if the concentration of a plurality of gases is intended to be ascertained, it is possible to use an adjustable filter with adjustable transmission properties. During the operation, the transmission properties of the filter 112 can be modified successively in order successively to excite gas molecules of different gases to be analysed. The filter may be embodied as a plasmonic filter or as a Fabry-Perot interferometer, such as a Fabry-Pérot etalon.

The gas analysis apparatus 100 can be used to monitor the composition of the ambient air, for example for ascertaining the $CO_2$ content or the content of toxic gases, such as CO, in the ambient air. Moreover, it is possible to ascertain the methane content of ambient air or ascertain the humidity herewith. The use as a breathalyser for ascertaining the alcohol content in the breath of a test person or for ascertaining the acetone content in the breath of a test person is also conceivable. The acetone content can be used for ascertaining the blood sugar level.

As indicated in FIG. 1, the gas chamber 102 may be delimited by a gas chamber wall 114. A passage opening 116, serving as gas inlet or as gas outlet, may be provided in the gas chamber wall 114. The passage opening 116 may be open at least intermittently or else permanently. In this way, the gas chamber 102 may have, at least intermittently or else permanently, a gas exchange connection with the surroundings 118 of the gas analysis apparatus 100. As result of this, a gas exchange, for example by diffusion, may be ensured between the gas chamber 102 and the surroundings 118 of the gas analysis apparatus 100 in order to monitor the composition of the ambient air.

Figure 2:
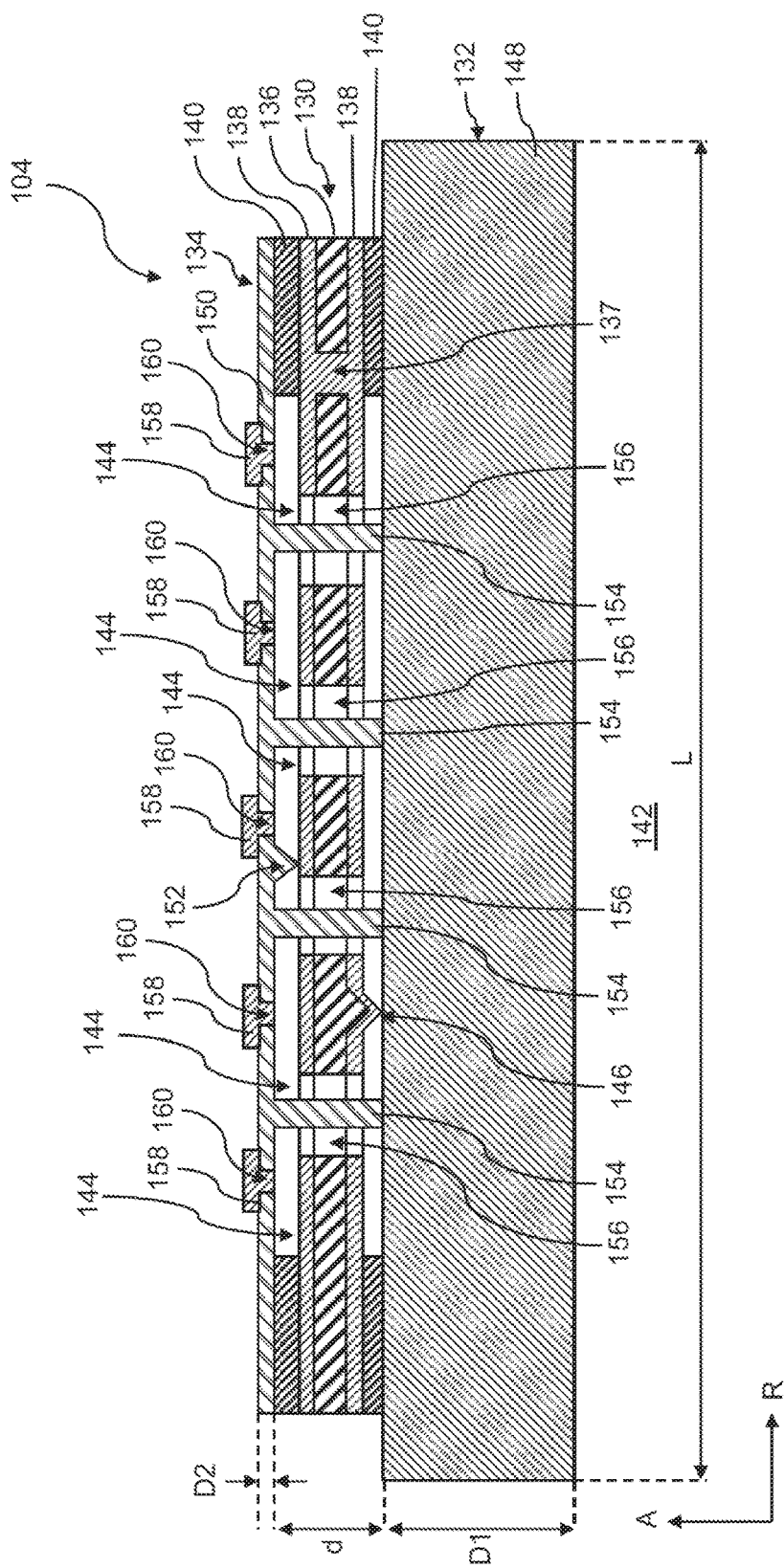
FIGS. 2 to 11 show schematic illustrations of various embodiments of a radiation source for a gas analysis apparatus illustrated in FIG. 1.

FIG. 2 is a schematic cross-sectional illustration of an exemplary radiation source 104 for a gas analysis apparatus. The radiation source 104 has an electrically heatable planar radiation element 130 and a first planar housing wall 132 and a second planar housing wall 134. The radiation element 130 is configured to emit electromagnetic radiation. The first housing wall 132 and/or second housing wall 134 is/are configured to transmit electromagnetic radiation that is emittable by the radiation element 130.

The radiation element 130 may have a layer structure with an electrically conductive layer 136 which, in the thickness direction of the radiation element 130, is received between two electrically insulating layers 138. The electrically conductive layer 136 may be formed from a metal or from polycrystalline silicon (polysilicon). The electrically insulating layers may be formed from a dielectric, such as, for instance, from $SiO_2$ or $Si_3N_4$. As indicated in FIG. 2, the electrically conductive layer 136 may have at least one passage opening 137 in the thickness direction, which is filled with electrically insulating material, for instance the electrically insulating material of the electrically insulating layer 138. As a result of this, it is possible to define a defined conductor track in the electrically conductive layer 136.

Figure 3:
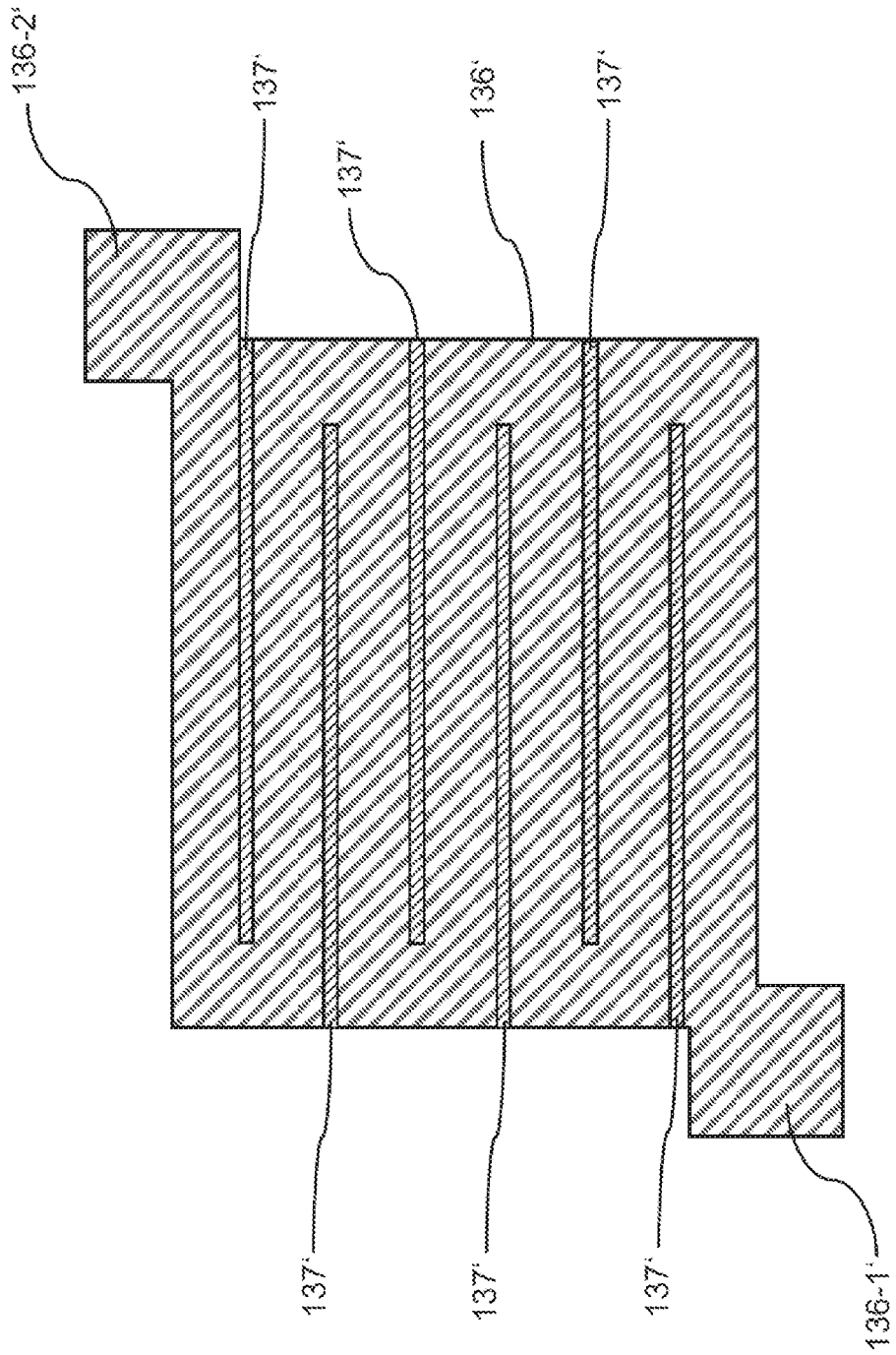

This is shown schematically in FIG. 3. The exemplary electrically conductive layer 136', shown in FIG. 3, has a plurality of elongate openings 137' that are arranged substantially parallel to one another, said openings being filled with an electrically insulating material. As a result, a meandering conductor track is formed between two contacting regions 136-1', 136-2' of the electrically conductive layer 136', the length of which is longer when compared to an electrically conductive layer without the openings. As a result, there is also an increase in the electrical resistance of the electrically conductive layer between the contacting regions 136-1', 136-2'. Naturally, the configuration shown in FIG. 3 is not intended to be restrictive. Rather, the electrically conductive layer of a radiation element can have virtually any structuring in order to set the electrical resistance of the layer to a desired value.

The radiation element 130 may be embodied as a black-body emitter and may be electrically heated to temperatures of more than 450° C. during operation, as explained in conjunction with the gas analysis apparatus 100 described in FIG. 1. Therefore, there may be a thermally induced deformation of the radiation element 130 and, possibly, short circuits between the radiation element 130 and, for example, one of the housing walls 132, 134. As a result of the layer structure of the radiation element 130, i.e. as a result of the electrically insulating layers 138, it is possible to effectively prevent short circuits, even in the case of a thermally induced deformation of the radiation element 130.

At a radially outer section, the radiation element 130 may be connected at an axial side to the first housing wall 132 in a fluid-tight manner, e.g. in a gas-tight manner, by means of a connection element 140 and it may be connected at the opposite axial side to the second housing wall 134 in a fluid-tight manner, e.g. in a gas-tight manner, by means of a further connection element 140. The connection elements 140 may extend continuously in the circumferential direction and may have a substantially ring-shaped form. In FIG. 2, the radial direction and the axial direction are indicated by the reference signs R and A, respectively.

On account of the ring-shaped form of the connection elements 140, a radiation element receptacle chamber 144, which is separated from the surroundings 142 of the radiation source 104 in a fluid-tight manner, e.g. in a gas-tight manner, may be formed, said radiation element receptacle chamber being immediately delimited by the first housing wall 132 and the second housing wall 134 in the axial direction and receiving a section of the radiation element 130.

A gas pressure which is lower than the normal pressure (1013.25 mbar) prevails in the radiation element receptacle chamber 144. In an embodiment, the gas pressure in the radiation element receptacle chamber 144 is less than 100 mbar, optionally less than 50 mbar, as a further option less than 10 mbar. In this way, it is possible to reduce the thermal conductivity between the radiation element 130 and the first housing wall 132 and the second housing wall 134, respectively, in comparison with an otherwise identical radiation source 104, in which, however, a higher gas pressure is prevalent in the radiation element receptacle chamber 144. As a result of this, it is possible to avoid an inadvertent excitation of gas molecules of gases that are not to be analysed.

Moreover, the thermal conductivity between the radiation element 130 and one of the two housing walls 132, 134 may be reduced by virtue of the radiation element 130 being spaced apart from the first housing wall 132 and/or the second housing wall 134 in the radiation element receptacle chamber 144. As shown in FIG. 2, the electrically insulating layers 138 of the radiation element 130 may be spaced apart from the first housing wall 132 and second housing wall 134, respectively.

As indicated in FIG. 2, the radiation element 130 may have an anti-adhesion protrusion 146 at an axial side, said anti-adhesion protrusion tapering with increasing distance from the radiation element 130. The anti-adhesion protrusion 146 prevents the radiation element 130 from adhering if it bulges in the direction of the first housing wall 132 for thermal reasons and if comes into contact with the latter since the contact area with the first housing wall 132 is reduced in comparison with a radiation element 130 without an anti-adhesion protrusion 146.

Even if FIG. 2 only shows a single anti-adhesion protrusion 146 at the radiation element 130, provision can naturally also be made of a plurality of anti-adhesion protrusions at an axial side of the radiation element 130. Likewise, a radiation element 130 with anti-adhesion protrusions at both axial sides is conceivable. At least one anti-adhesion protrusion can have an integral embodiment with the electrically conductive layer 136 and/or an electrically insulating layer 138 of the radiation element 130.

The first housing wall 132 may have a substrate 148 which is formed from material that is transparent to at least one wavelength range of the spectrum that is emittable by the radiation element 130. In an embodiment, the substrate is produced from a semiconductor, for instance monocrystalline silicon or germanium. The first housing wall 132 may have a thickness D1 of more than 10 μm. The radiation element 130 may have a length L of less than 1 mm.

The second housing wall 134 may likewise have a substrate 150 that is formed from a material that is transparent to at least one wavelength range of the spectrum that is emittable by the radiation element 130. Here too, a substrate 150 formed from a semiconductor, for instance monocrystalline silicon or germanium, is conceivable. In an embodiment, the substrate 150 may be formed from polysilicon or a dielectric, for instance $SiO_2$. The second housing wall 134 may also have a thickness D2 of more than 10 μm. Alternatively, it may have a lower thickness in order to increase, in comparison with a thicker second housing wall, the transmissivity for electromagnetic radiation that is emittable by the radiation element 130.

The distance d between the first housing wall 132 and the second housing wall 134, i.e. the extent of the radiation element receptacle chamber 104 in the axial direction A, may be less than 10 μm, optionally less than 5 μm, as a further option less than 1 μm. As a result of the first housing wall 132 and the second housing wall 134 and also the radiation element 130 being planar, such a distance d between the first housing wall 132 and the second housing wall 134 renders it possible to ensure that more radiation is emitted in the axial direction A than in the radial direction R in the case of the same heating power. As a result, electromagnetic radiation can be efficiently emitted in the axial direction A, and so gas molecules of a gas to be analysed in the gas chamber 102 can be excited efficiently in the case of a gas chamber 102 of a gas analysis apparatus positioned at an axial side of the radiation source 104.

As shown in FIG. 2, the second housing wall 134 may also be provided with an anti-adhesion protrusion 152, which protrudes into the radiation element receptacle chamber 144 and which tapers with increasing distance from the substrate 150. The anti-adhesion protrusion 152 may have an integral embodiment with the substrate 150. Naturally, a plurality of anti-adhesion protrusions 152 may be provided, too. Anti-adhesion protrusions may also be provided at the first housing wall 132.

Further, the radiation source 104 may have at least one spacer 154, arranged in the radiation element receptacle chamber 144, between the first housing wall 132 and the second housing wall 134. As shown in FIG. 2, it may also be the case that a plurality of such spacers 154 are provided, which, for example, may be provided with distances of 20 μm from one another. As a result of the spacers 154, it is possible to ensure a defined distance d between the first housing wall 132 and the second housing wall 134. As a result, one of the housing walls 132, 134 may be embodied with a lower thickness in order to be able to ensure a higher transmissivity for electromagnetic radiation that is emittable by the radiation element 130.

At least one spacer 154 may have permanent physical contact with the first housing wall 132 and/or the second housing wall 134 or may even have an integral embodiment with the first housing wall 132 and/or the second housing wall 134. In the exemplary embodiment shown in FIG. 2, the spacers 154 have an integral embodiment with the second housing wall 134. As shown in FIG. 2, at least one spacer 154, or all spacers 154, may be completely received in the radiation chamber 144. Here, "completely received" states that no section of the spacer 154 is exposed to the surroundings 142 of the radiation source 104.

In the exemplary radiation source 104 shown in FIG. 2, the radiation element 130 respectively has, assigned to the spacers 154, a continuous passage opening 156 that extends in the thickness direction of the radiation element 130, the respective spacers 154 extending through said passage opening. The diameters of the respective passage openings 156 may be greater than the diameters of the spacers 154. As a result of this, physical contact between the spacers 154 and the radiation element 130 may be prevented, i.e. the spacers 154 may be positioned at a distance from the radiation element 130. As a result, the thermal conductivity between the radiation element 130 and the first housing wall 132 and second housing wall 134 may be reduced.

As shown in FIG. 2, one of the housing walls 132, 134, for example the second housing wall 134, may have a plurality of sealing element 158 which seal a plurality of openings 160 in the substrate 150 of the second housing wall 134. The openings 160 may have production-related origins, which will still be discussed in detail below.

A radiation source according to a second embodiment is described below with reference to FIG. 4. The radiation source 204 shown in FIG. 4 differs from the radiation source 104 shown in FIG. 2 merely in view of the configuration of the second housing wall 234. In the second embodiment, the second housing wall 234 has a substrate 250 which may have a similar structure to the substrate 150 of the radiation source 104 according to the first embodiment. Moreover, the second housing wall 234 also has a filter 262 which is configured to transmit, in a wavelength-selective manner, the electromagnetic radiation that is emittable by the radiation element 230.

Figure 4:
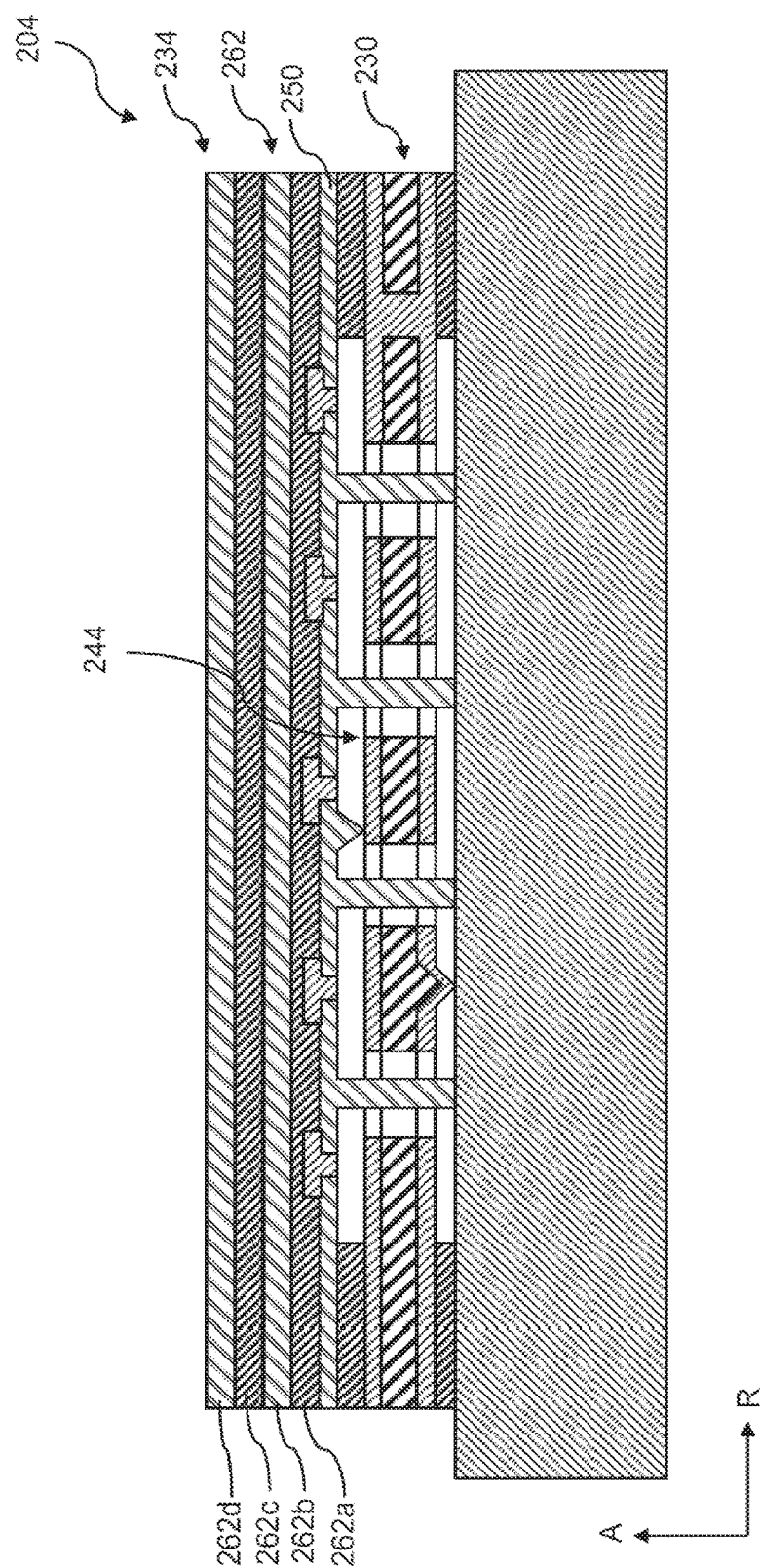

The filter 262 may have fixedly set transmission properties and may, as indicated in FIG. 4, have a plurality of layers 262a, 262b, 262c, 262d, of which at least two layers may have refractive indices and/or thicknesses that differ from one another. By way of example, the layers 262a, 262b, 262c, 262d may be formed from $SiO_2$ and/or polysilicon. Here, an alternating sequence of $SiO_2$ and polysilicon layers is conceivable. By way of the filter 262, it is possible to obtain the same technical effect as with the filter 112 discussed in conjunction with FIG. 1. Here, the substrate 250 of the second housing wall 234 may also be embodied as a filter layer, which immediately delimits the radiation element receptacle chamber 244.

Figure 5:
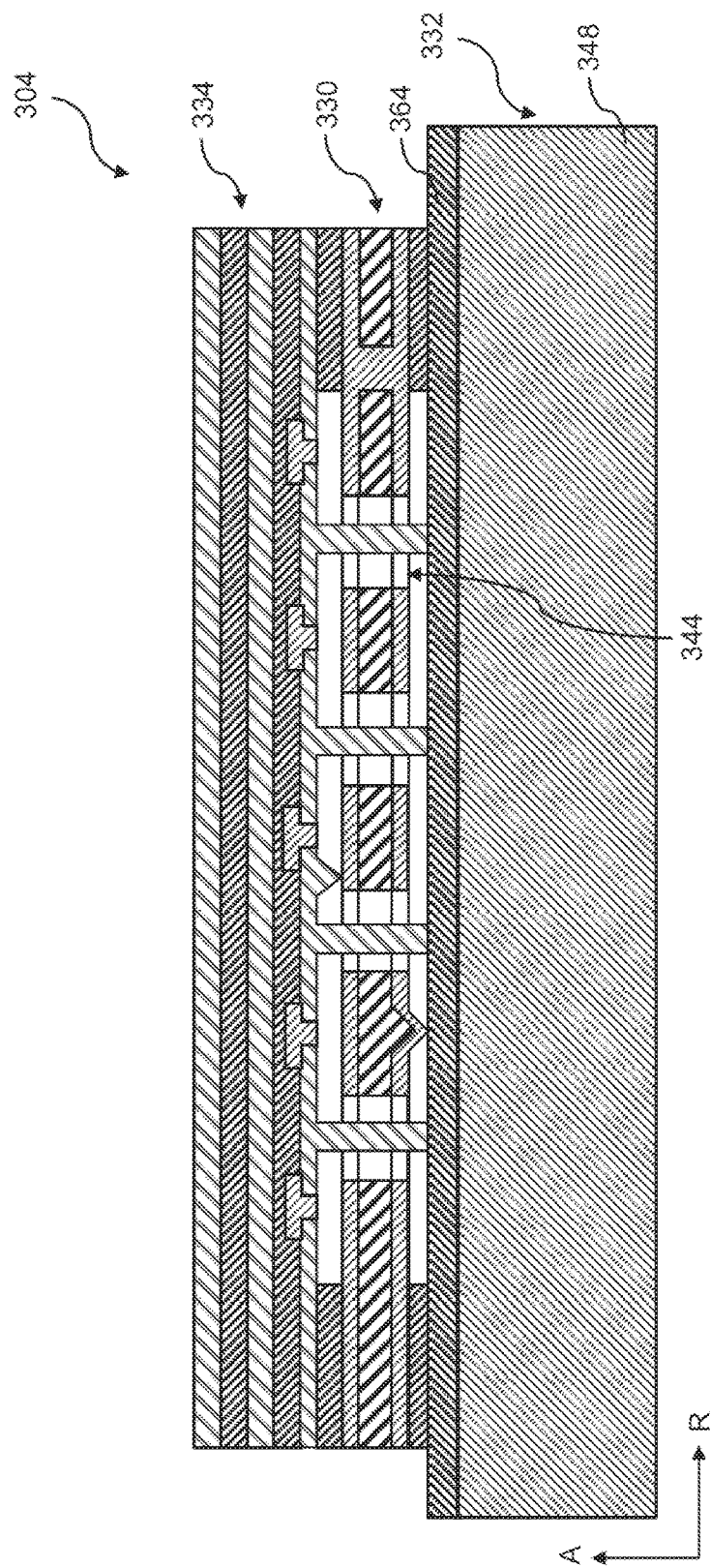

A radiation source according to a third embodiment will be described below with reference to FIG. 5. The radiation source 304 according to the third embodiment merely differs from the radiation source 204 according to the second embodiment in respect of the structure of the first housing wall 332. In contrast to the second embodiment, said housing wall additionally has a reflector 364 in addition to a substrate 348. As indicated in FIG. 5, the reflector 364 is embodied as a planar component and provided on an axial side of the substrate 348 facing the radiation element receptacle chamber 344. The reflector 364 may have a metallic layer, for instance made of aluminium, or may be embodied as such.

The reflector 364 may have a reflectance of at least 0.2, optionally of at least 0.5, as a further option at least 0.8, in the infrared frequency range and/or in the visible frequency range and/or in the ultraviolet frequency range.

By way of the reflector 364, the electromagnetic radiation that is emittable by the radiation element 330 may be output coupled in a targeted manner merely through the second housing wall 334.

Figure 6:
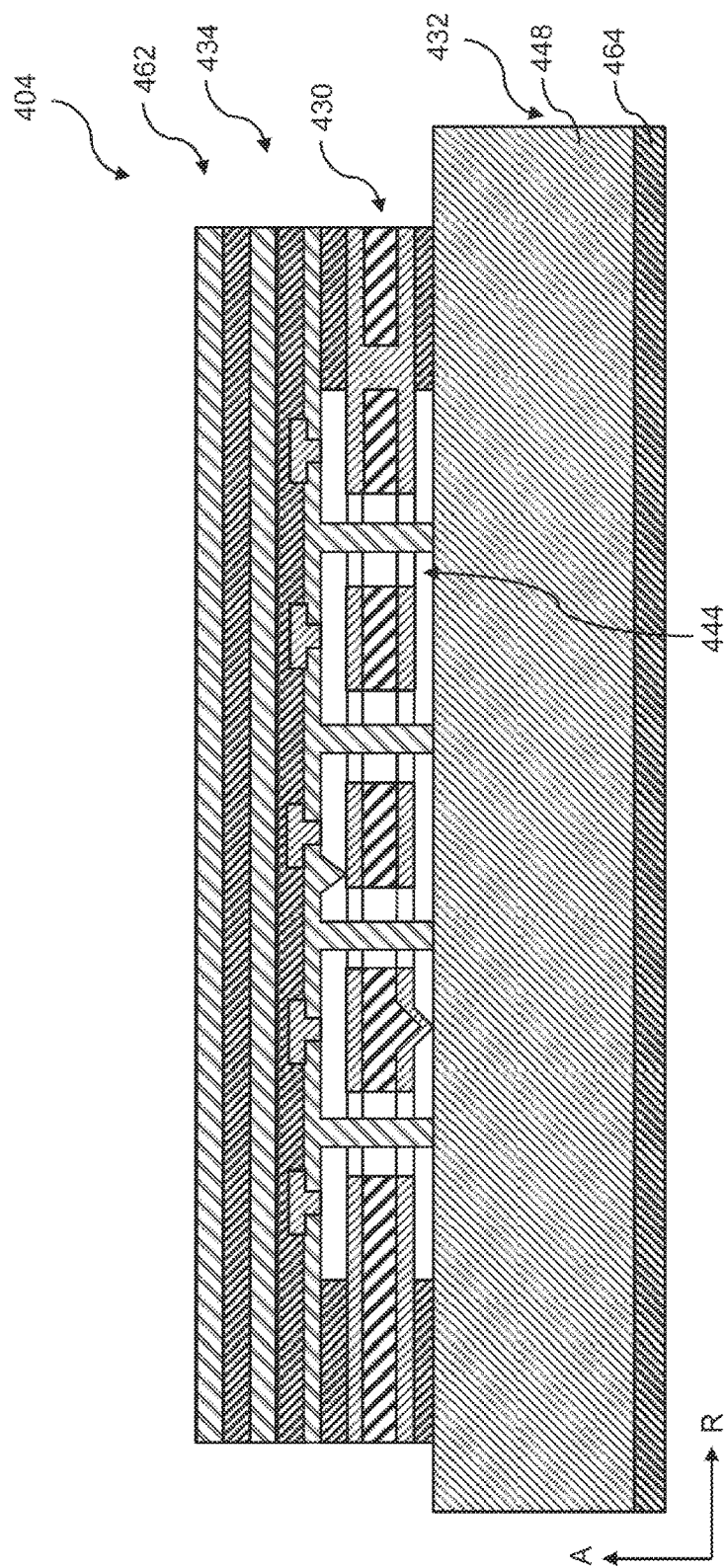

A radiation source according to a fourth embodiment will be described below with reference to FIG. 6. The radiation source 404 according to the fourth embodiment merely differs from the radiation source 304 according to the third embodiment in respect of the positioning of the reflector 464. In contrast to the third embodiment, said reflector is provided on an axial side of the substrate 448 of the first housing wall 432 that faces away from the radiation element receptacle chamber 444. The provision of the reflector 464 according to the fourth embodiment is particularly suitable when the substrate 448 of the first housing wall 432 is formed from a material which transmits at least a wavelength range of the spectrum that is emittable by the radiation element 430. By way of example, the substrate 448 can be formed from a semiconductor, for example silicon, which is transmissive for infrared radiation.

Consequently, the first housing wall 432 is delimited in the axial direction A by the reflector 464 and the second housing wall 462 is delimited in the axial direction by the filter 462. As a result of this, electromagnetic radiation that is emittable by the radiation element 430 can be output coupled through the second housing wall 434 in a targeted manner.

Figure 7:
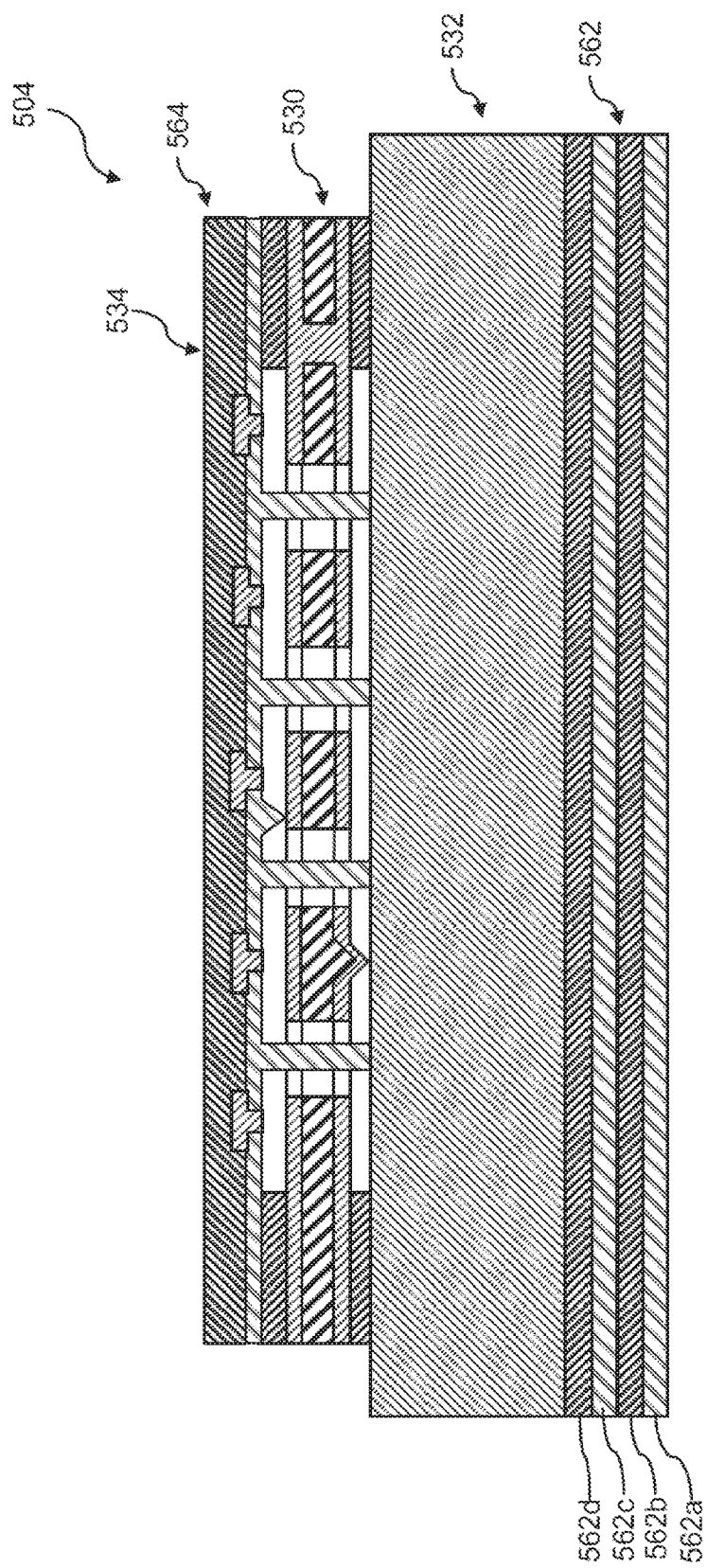

A radiation source according to a fifth embodiment will be described below with reference to FIG. 7. The radiation source 504 according to the fifth embodiment merely differs from the radiation source 404 according to the fourth embodiment in that the first housing wall 532 is delimited in the axial direction A by a filter 562 having a plurality of layers 562a, 562b, 562c, 562d and in that the second housing wall is delimited in the axial direction by a reflector 564, for instance a metallic reflector 564. In this way, electromagnetic radiation that is emittable by the radiation element 530 can be output coupled through the first housing wall 532 in a targeted manner.

Figure 8:
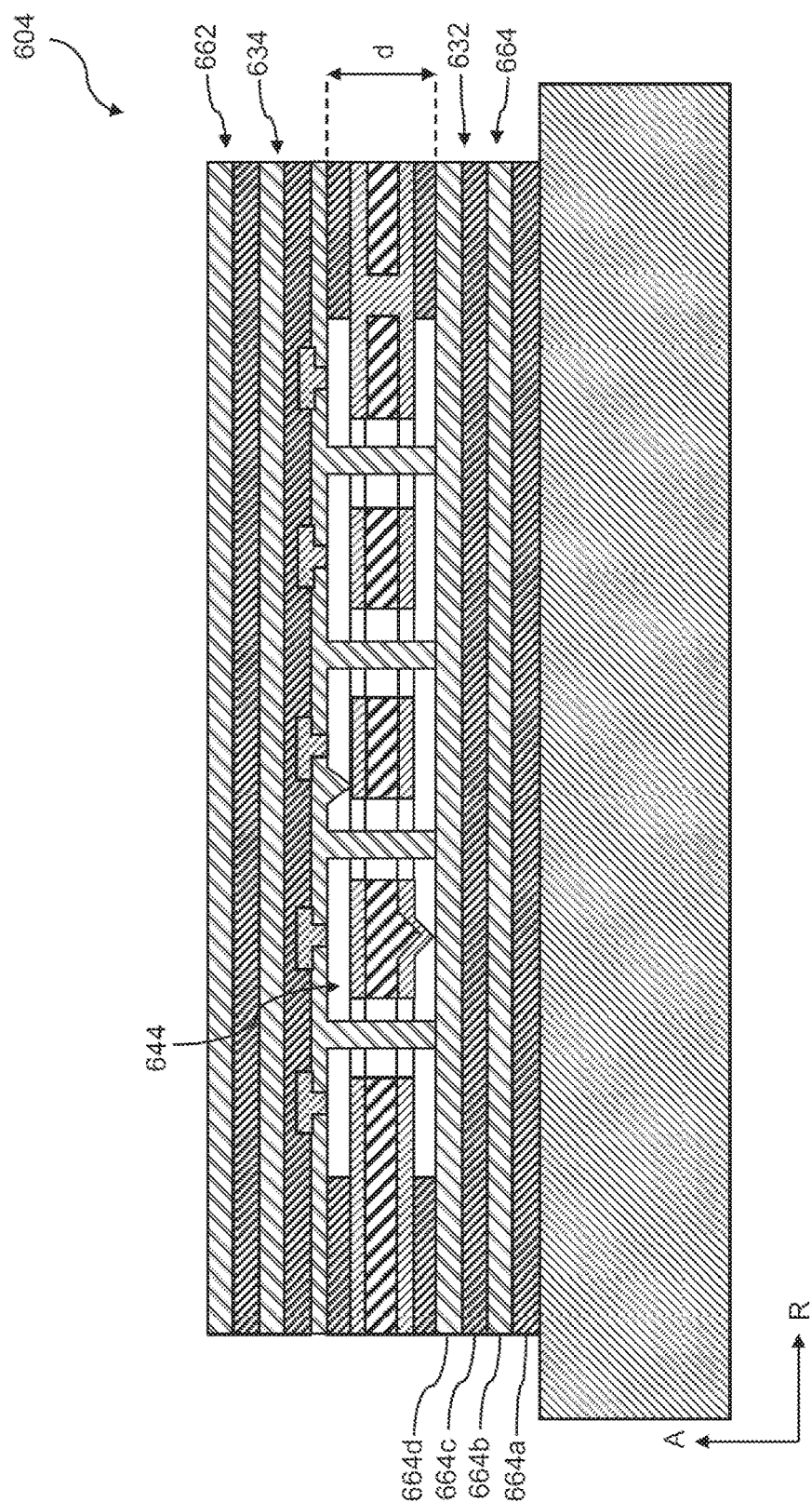

A radiation source according to a sixth embodiment will be described below with reference to FIG. 8. The radiation source 604 according to the sixth embodiment differs from the radiation source 304 according to the third embodiment in respect of the design of the reflector 664. In contrast to the third embodiment, said reflector is embodied as a Bragg reflector and has a plurality of layers 664a, 664b, 664c, 664d, at least two of which layers may have refractive indices and/or layer thicknesses that differ from one another.

This configuration, in particular, offers the option of designing the radiation element receptacle chamber 644 as a resonator, in which it is possible to produce standing waves with a specific wavelength. Electromagnetic radiation at this wavelength can be output coupled with a high intensity in order to excite well-defined states of gas molecules of a gas to be analysed. The desired wavelength can be adjusted by means of the distance d between the reflector 664 of the first housing wall 632 and the filter 662 of the second housing wall 634. Then, it is possible to produce a standing wave with a predetermined wavelength λ, when the distance d between the first housing wall 632 and the second housing wall 634 equals an integer multiple of the half wavelength λ:

$$d = n\lambda/2,$$

where n is a natural number. This relationship can be set particularly easily if the radiation element receptacle chamber 644 is immediately delimited by the filter 662 and the reflector 664, as shown in FIG. 8. Naturally, the predetermined wavelength λ, must lie in the transmission range of the filter 662 so that electromagnetic radiation at this wavelength can be output coupled through the filter 662.

Figure 9:
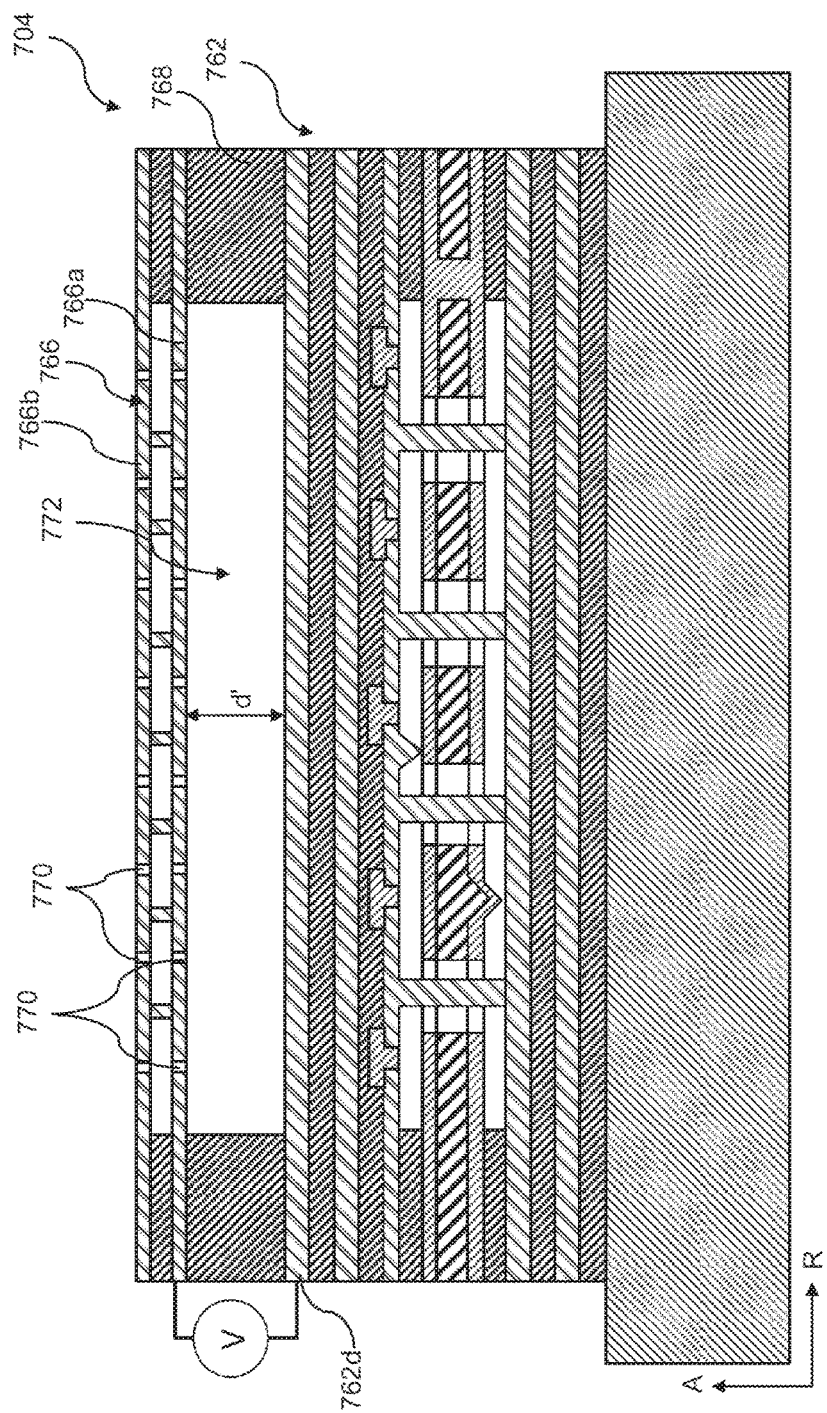

The radiation source 704 according to a seventh embodiment, shown in FIG. 9, differs from the radiation source 604 according to the sixth embodiment in that it additionally has an adjustable filter 766 which is arranged on a side of the filter 762 facing away from the radiation element receptacle chamber 744, said latter filter being a filter with fixedly predetermined transmission properties.

The adjustable filter 766 has a layer 762d of the filter 762 with fixedly predetermined transmission properties and at least one filter layer 766a, 766b, or even a plurality of filter layers, arranged at a distance d' therefrom. The filter layers 766a, 766b are separated from the layer 762d of the filter 762 by means of a connection structure 768. As indicated in FIG. 9, the connection structure 768 may have a substantially ring-shaped design. By way of example, the connection structure 768 may be formed from a dielectric, for instance $SiO_2$.

The layer 762d of the filter 762 with fixedly predetermined transmission properties and the filter layers 766a, 766b spaced apart therefrom may be formed from an electrically conductive material, for instance polysilicon. This offers the option of adjusting the distance d' by means of an electrical voltage V. As a result, the distance d' can be adjusted in a targeted manner to an integer multiple of half a predetermined wavelength λ, by means of the electrical voltage V by virtue of applying an electrical voltage to the layer 762d and to one of the filter layers 766a, 766b. This relationship can be expressed by the relationship:

$$d'(V) = n\lambda/2.$$

Consequently, it is possible to produce a standing wave with a well-defined wavelength by means of the adjustable filter 766 since the distance, relevant to this end, between the layer 762d and the filter layers 766a, 766b can be adjusted in a targeted manner by the electrical voltage V, and so possible tolerances, due to the production process, of the distance between the layer 762d and the filter layers 766a, 766b in a voltage-free state can be corrected where necessary.

The openings 770, shown in FIG. 9, in the filter layers 766a, 766b are openings which are used for etching the cavity 772 provided between the layer 762d and the filter layers 766a, 766b.

Figure 10:
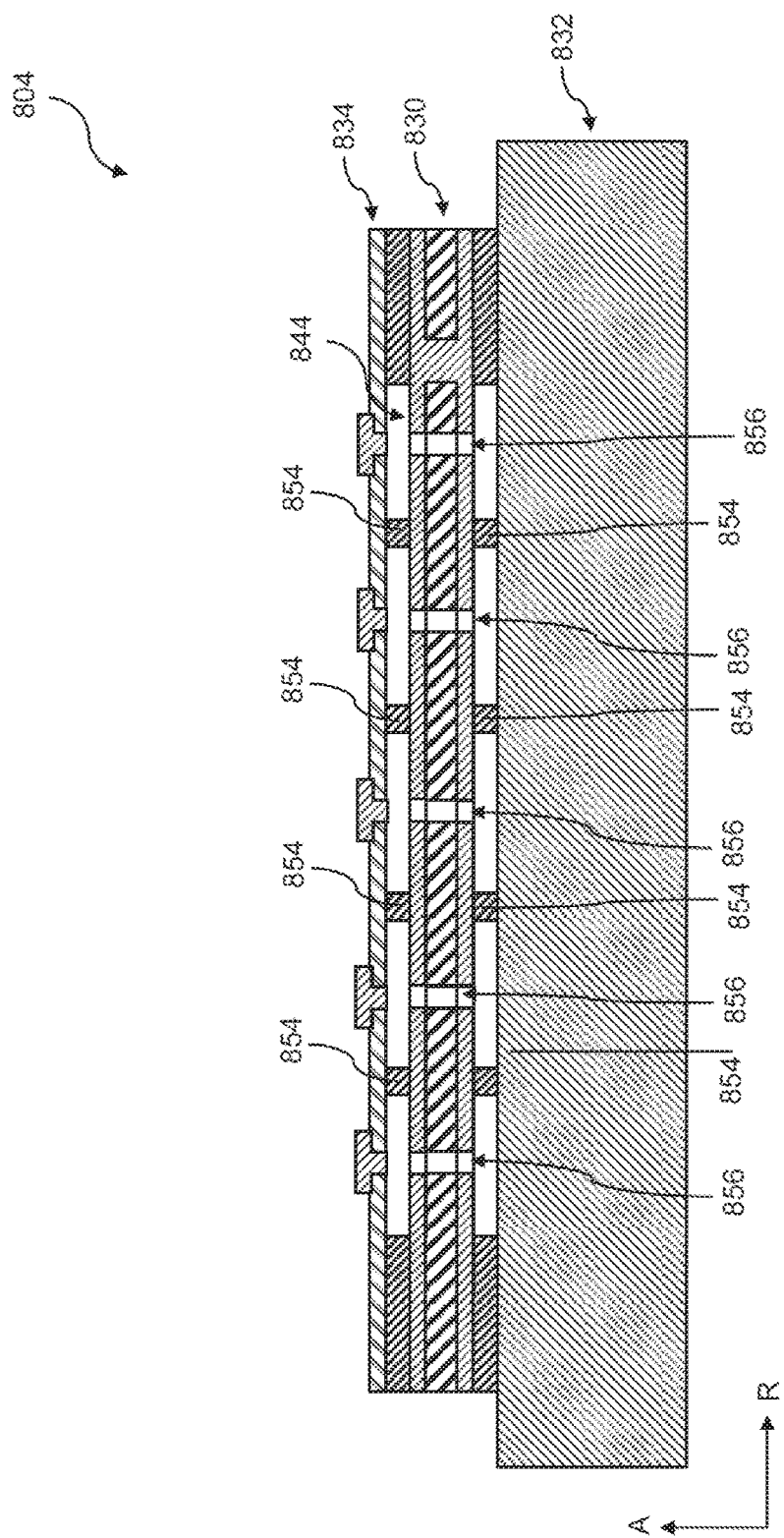

FIG. 10 illustrates a radiation source 804 according to an eighth embodiment. The radiation source 804 differs from the radiation source 104 according to the first embodiment in respect of the design of the spacers 854 between the first housing wall 832 and the second housing wall 834.

In contrast to the radiation source 104 according to the first embodiment, the spacers 854 have physical contact with the radiation element 830 in the radiation source 804 according to the eighth embodiment. As a result of this, it is possible to keep the distance constant not only between the first housing wall 832 and the second housing wall 834, but also between the radiation element 830 and the first housing wall 832 and second housing wall 834, respectively. By way of example, the spacers 854 can be embodied as webs which interconnect facing axial sides of the radiation element 830 and the first housing wall 832 and second housing wall 834, respectively. As shown in FIG. 10, the spacers 854 can be received entirely within a radiation element receptacle chamber 844.

The axial passage openings 856 in the radiation element 830, shown in FIG. 10, can be used as etching openings in order to etch the radiation element 830 free from the first housing wall 832 and the second housing wall 834 beyond the spacers 854.

Figure 11:
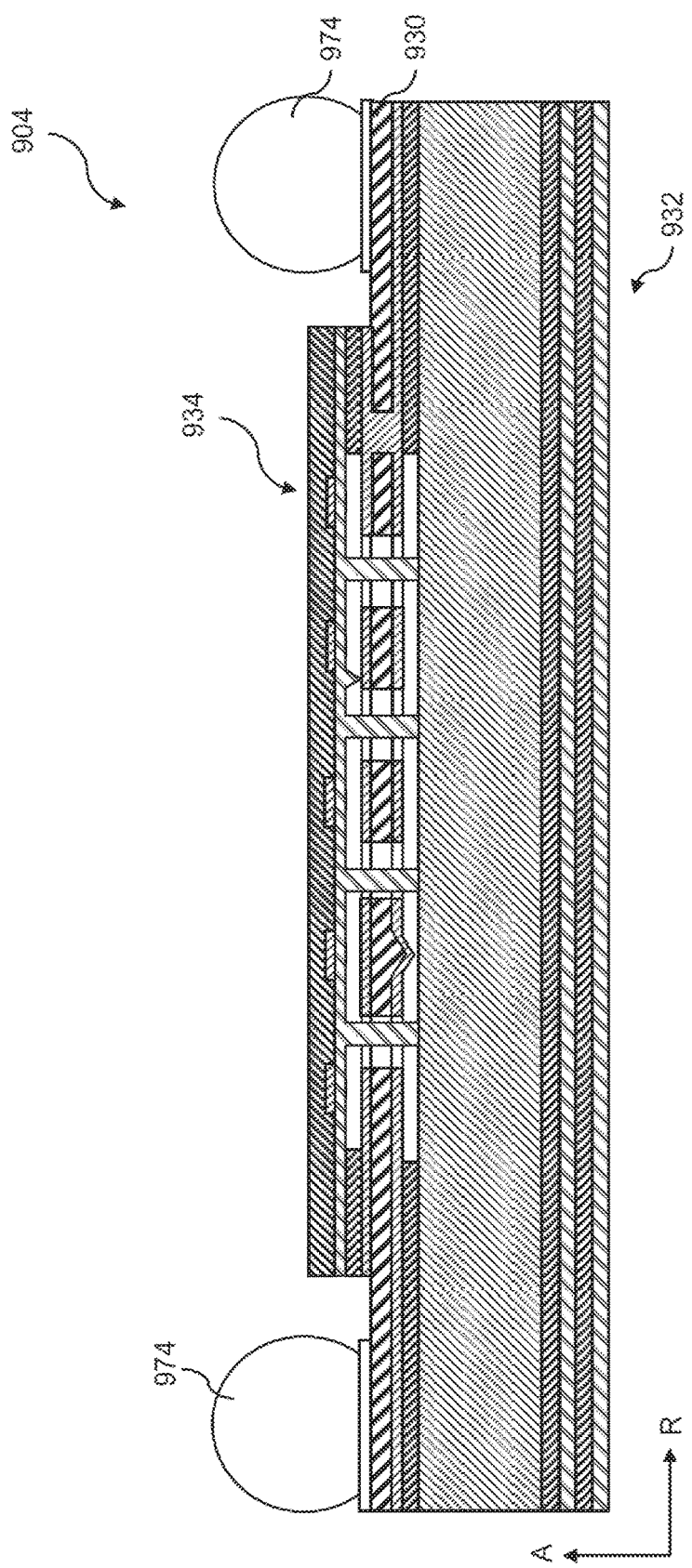

FIG. 11 shows a radiation source 904 according to a ninth embodiment. The radiation source 904 according to the ninth embodiment is similar to the radiation source 504 according to the fifth embodiment, shown in FIG. 7. In contrast to the radiation source 504, the first housing wall 932 and the radiation element 930 of the radiation source 904 have a greater radial extent than the second housing wall 934. The section of the radiation element 930 protruding beyond the second housing wall 934 in the radial direction can be used for electrical contacting of same, for instance with bumps 974.

Figure 12:
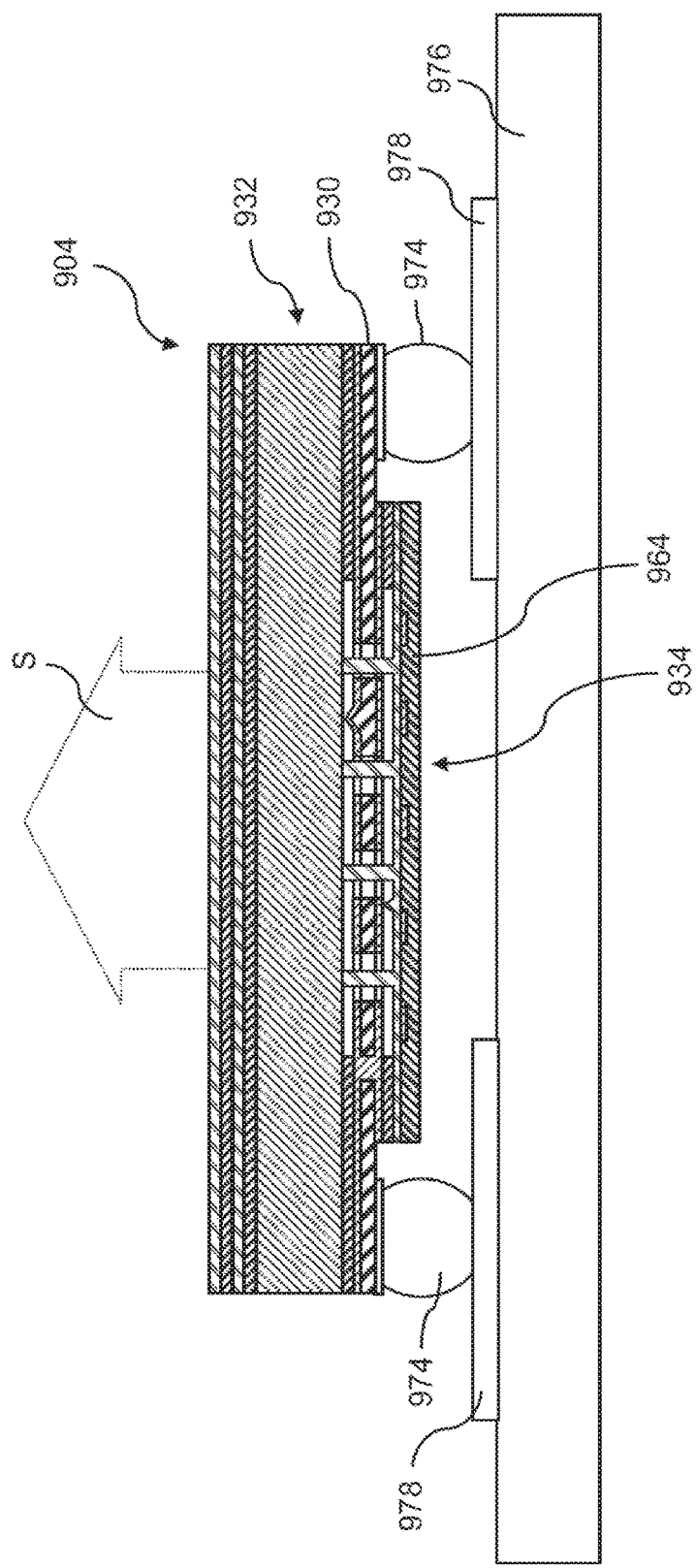
FIG. 12 shows the radiation source shown in FIG. 11 in a state assembled on a printed circuit board.

The radiation source 904 according to the ninth embodiment is suitable for a flip-chip assembly on a printed circuit board 976 shown in FIG. 12. To this end, the radiation source 904 is turned upside down from the position shown in FIG. 11 and placed onto the printed circuit board 976 in such a way that the bumps 974 come into contact with electrically conductive connectors 978 of the printed circuit board 976. The bumps 974 subsequently can be softened or liquefied, e.g. by means of hot air, in order to establish a permanent electrical connection with the connectors 978 after a subsequent solidification of the bumps 974.

In FIG. 12, S denotes the direction of the electromagnetic radiation that is emittable by the radiation element 930, said electromagnetic radiation merely being output coupled through the first housing wall 932 since an emergence of the electromagnetic radiation through the second housing wall 934 in the direction of the printed circuit board 976 is prevented by the reflector 964.

An exemplary method for producing a radiation source is described below on the basis of FIG. 13 to FIG. 23.

Figure 13:
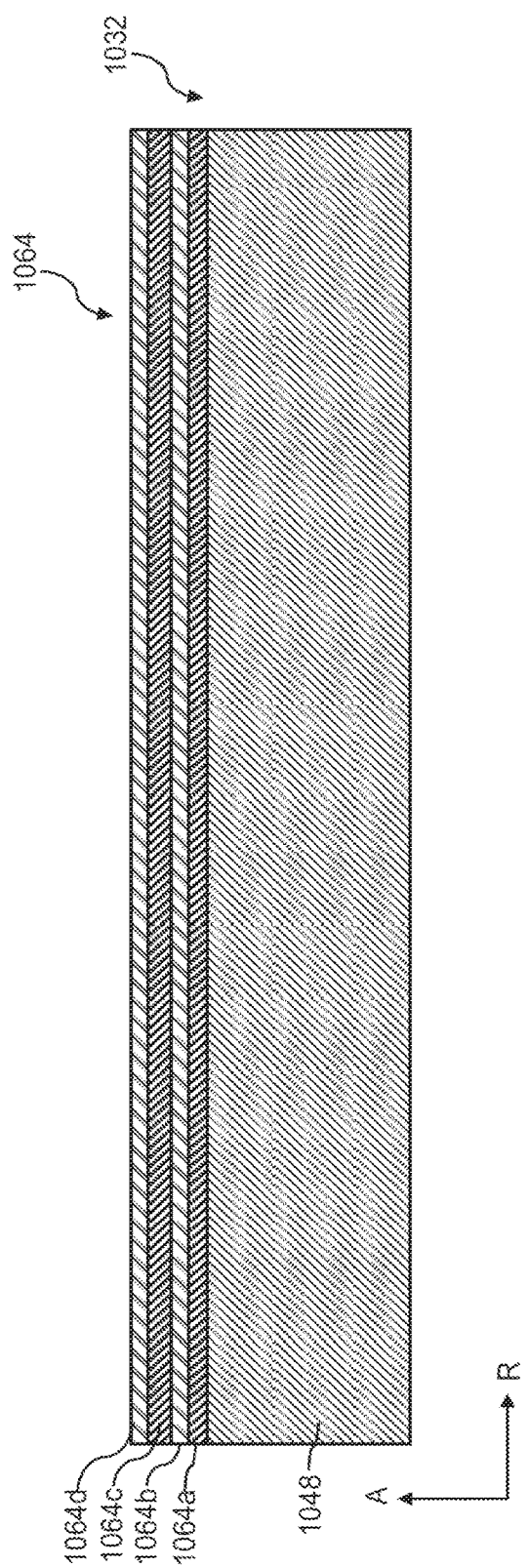
FIGS. 13 to 23 show an exemplary method for producing an exemplary radiation source.

The exemplary method may start with the provision of a substrate 1048, for instance made of a semiconductor material, for example monocrystalline silicon. As indicated in FIG. 13, it is possible to apply a plurality of layers 1064a, 1064b, 1064c, 1064d of a Bragg reflector 1064 onto this substrate 1048, for instance by chemical vapour deposition or sputtering. The layers 1064a and 1064c may be formed from $SiO_2$ and the layers 1064b and 1064d may be formed from polysilicon. The layers 1064a, 1064b, 1064c, 1064d may each have a thickness of $\lambda/4$, where $\lambda$, is the wavelength which is preferably reflected in the case of this layer structure by way of constructive interference. The production of a first housing wall 1032 is completed with the production of the Bragg reflector 1064 on the substrate 1048.

Figure 14:
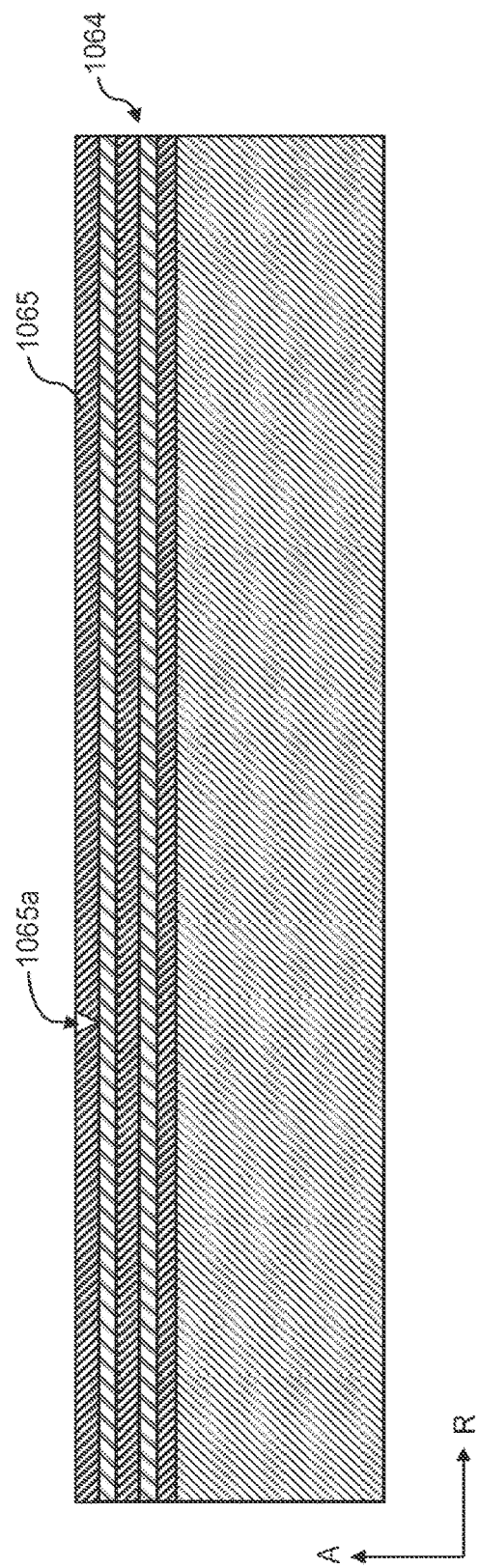

Subsequently, as shown in FIG. 14, a sacrificial layer 1065, for example made of $SiO_2$, may be applied to the Bragg reflector 1064, for instance by chemical vapour deposition. At least one opening 1065a can be formed therein, for example by etching. The opening 1065a can have a form which tapers in the direction of the Bragg reflector 1064 and may serve to form a spacer of a radiation element.

Figure 15:
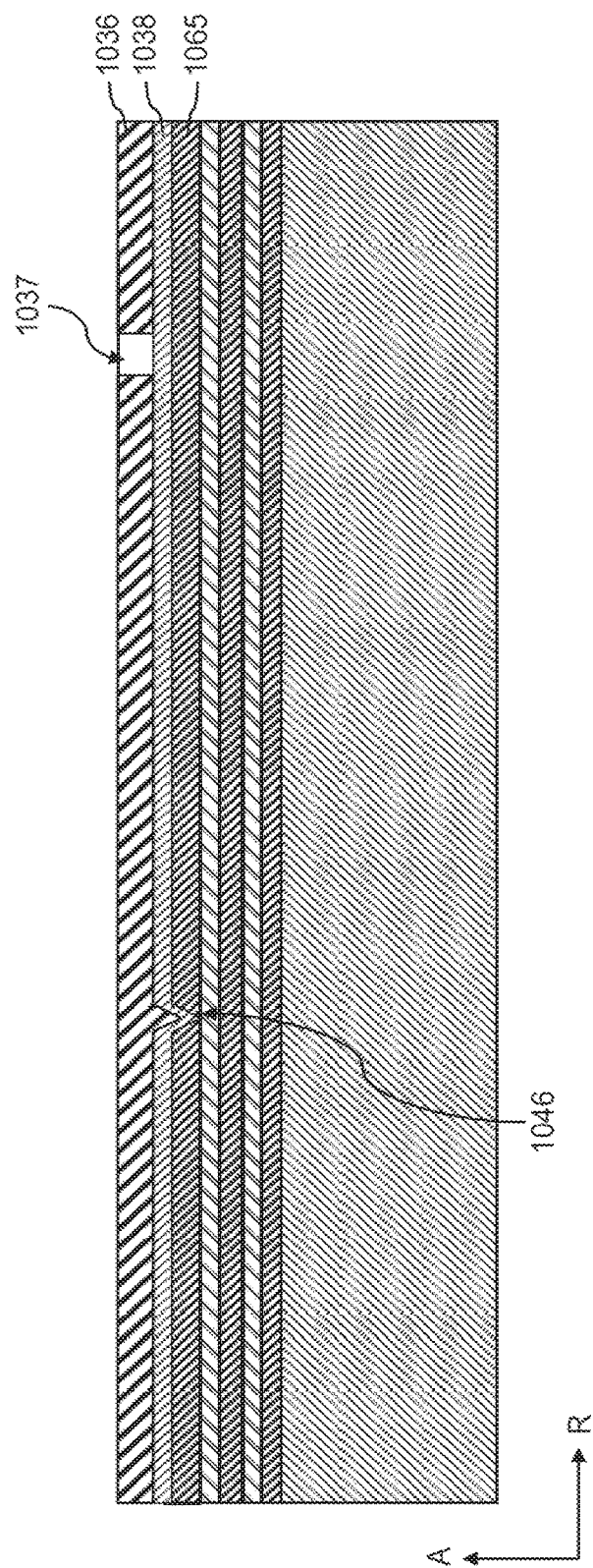

Subsequently, as shown in FIG. 15, an electrically insulating layer 1038, for instance a dielectric layer, may be applied onto the sacrificial layer 1065 and an electrically conductive layer 1036 may be applied onto the electrically insulating layer 1038. By way of example, the electrically insulating layer 1038 may be formed from $Si_3N_4$. The electrically conductive layer 1036 may be formed from a metal and/or polysilicon. Here, the at least one opening 1065a provided in the sacrificial layer 1065 may be filled, as a result of which a precursor of a spacer 1046 may be formed. Moreover, a passage opening 1037 may be formed in the conductive layer 1036, for example by etching. As described above, the passage opening 1037 may form e.g. a meandering form in the electrically conductive layer 1036 in order to be able to adjust the electrical resistance of this layer 1036.

Figure 16:
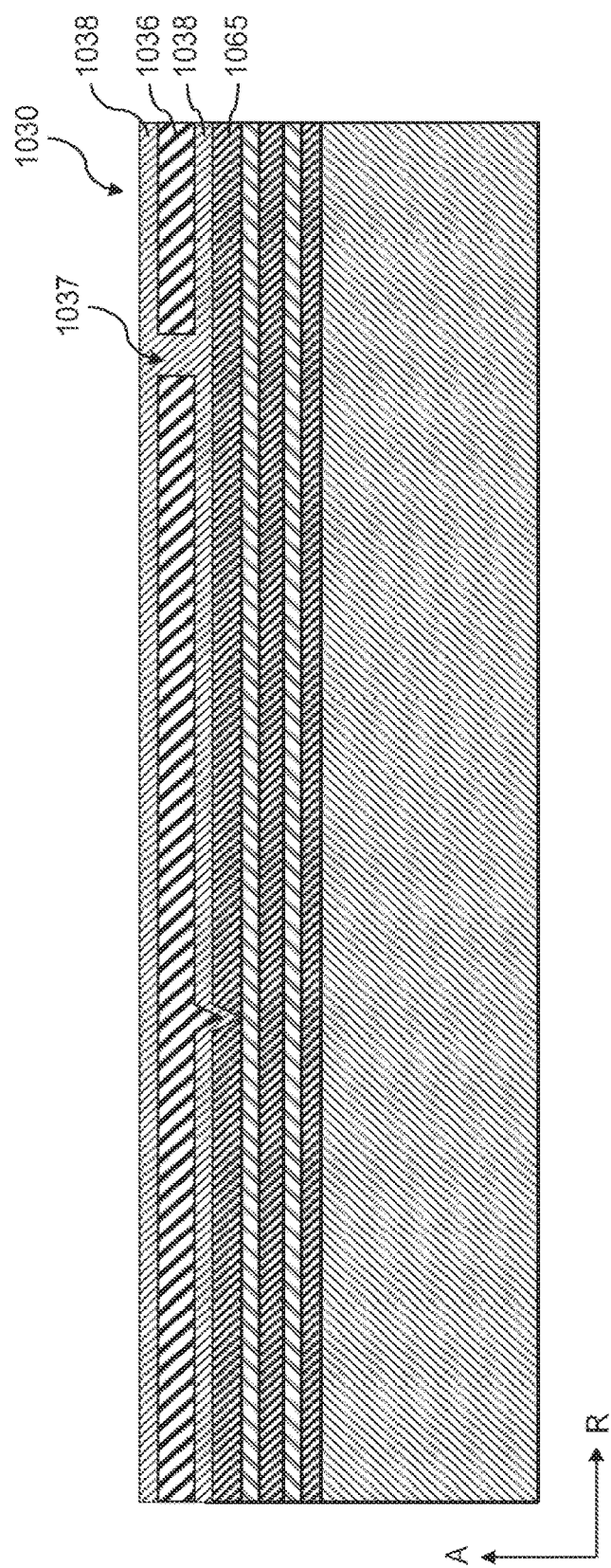

Subsequently, as shown in FIG. 16, a further electrically insulating layer 1038 may be applied onto the electrically conductive layer 1036, as a result of which the passage opening 1037 is filled with electrically insulating material, for instance $Si_3N_4$.

Figure 17:
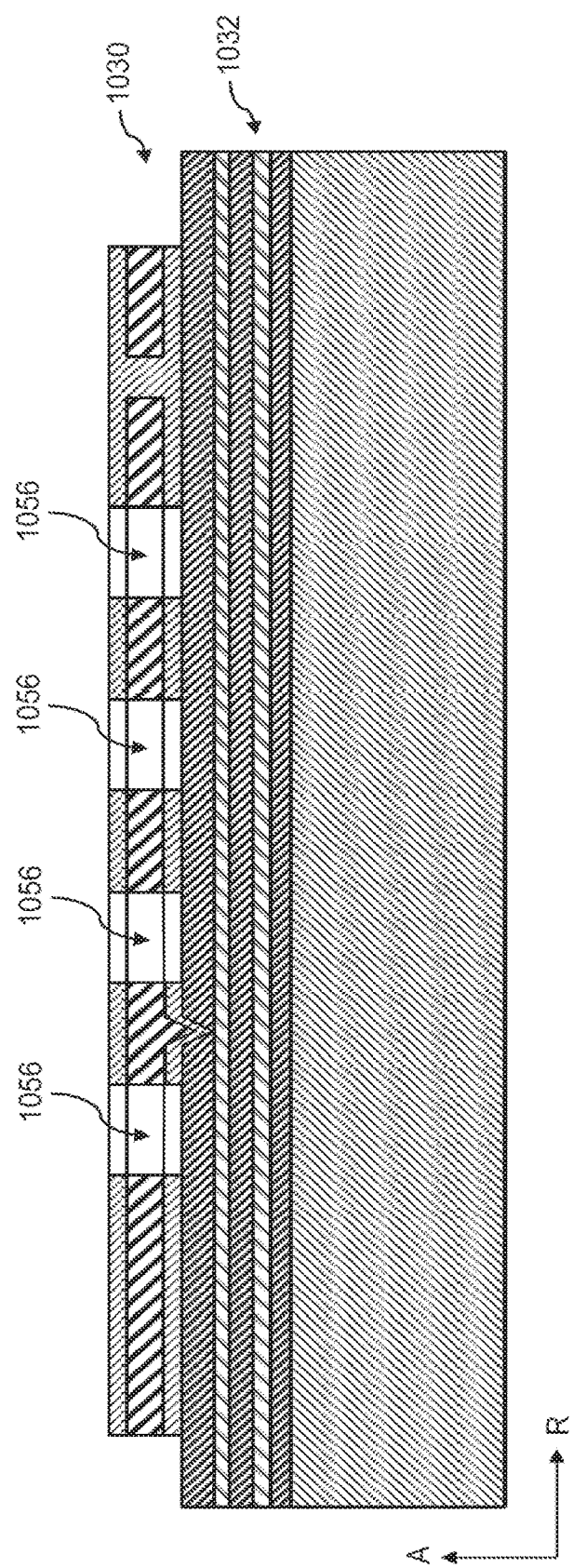

The layer stack made of the two electrically insulating layers 1038 and the electrically conductive layer 1036 received therebetween corresponds to a radiation element 1030, which can subsequently be structured further, as shown in an exemplary manner in FIG. 17. As shown in FIG. 17, it is possible during the subsequent structuring to form a plurality of passage openings 1056 for receiving spacers in the radiation element 1030. Here too, the radial extent of the radiation element 1030 can be reduced in comparison with the radial extent of the first housing wall 1032. The axial direction and radial direction are indicated in FIG. 17 by the reference signs A and R, respectively.

Figure 18:
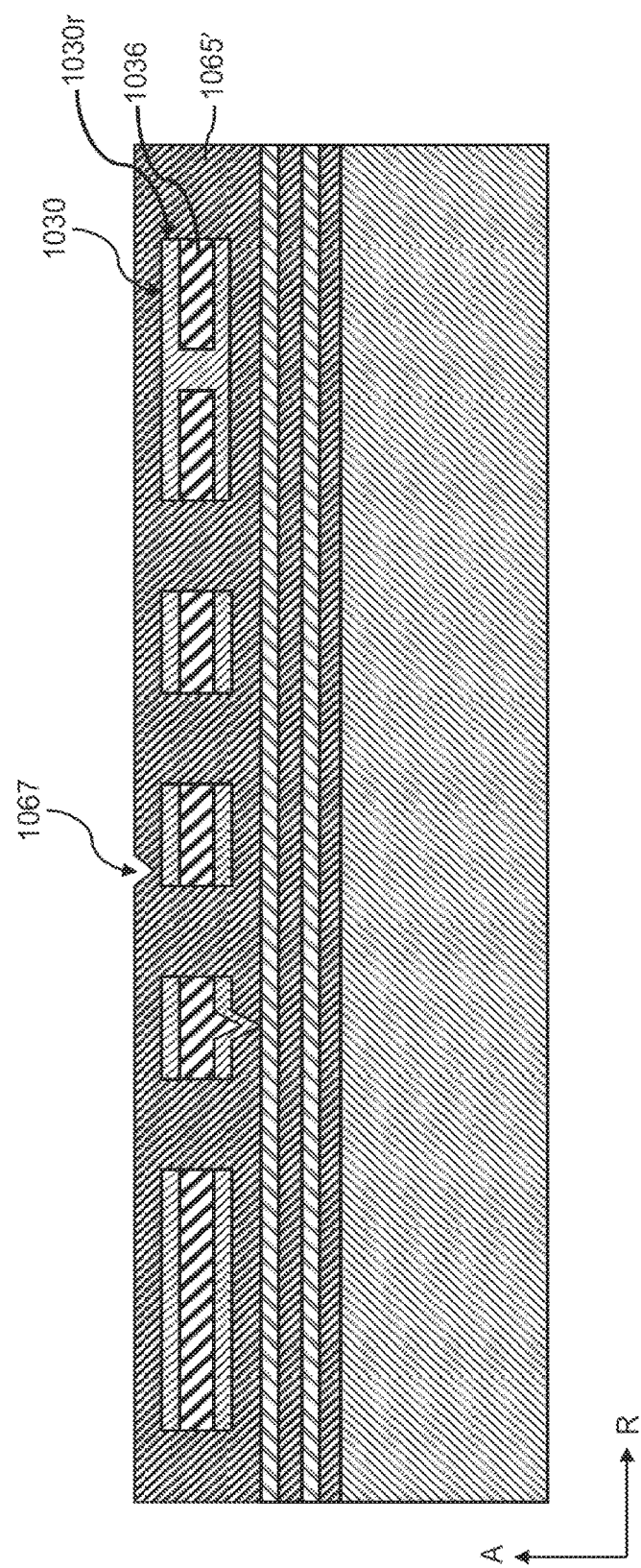

As shown in FIG. 18, the sacrificial layer 1065 can subsequently be complemented in the axial direction, i.e. a second sacrificial layer 1065' can be applied onto the sacrificial layer 1065 already present. The sacrificial layer 1065' may be formed from the same material as the first sacrificial layer 1065 and consequently form a uniform sacrificial layer 1065' together with the first sacrificial layer 1065.

As shown in FIG. 18, the sacrificial layer 1065' also can cover an edge region 1030r of the radiation element 1030 in order to electrically insulate the electrically conductive layer 1036 from all sides. Naturally, the radiation sources described above may be provided with a similar configuration. Moreover, a tapering opening 1067 can be formed in the sacrificial layer 1065', for example by etching, said opening serving to produce an anti-adhesion protrusion, described below, of a second housing wall. Even if only a single opening 1067 is shown in FIG. 18, a plurality of such openings 1067 naturally may be formed as well, said plurality of openings being able to be used for the formation of a plurality of anti-adhesion protrusions. The sacrificial layer 1065' can be provided with a plane surface facing away from the radiation element 1030 by chemical mechanical polishing.

Figure 19:
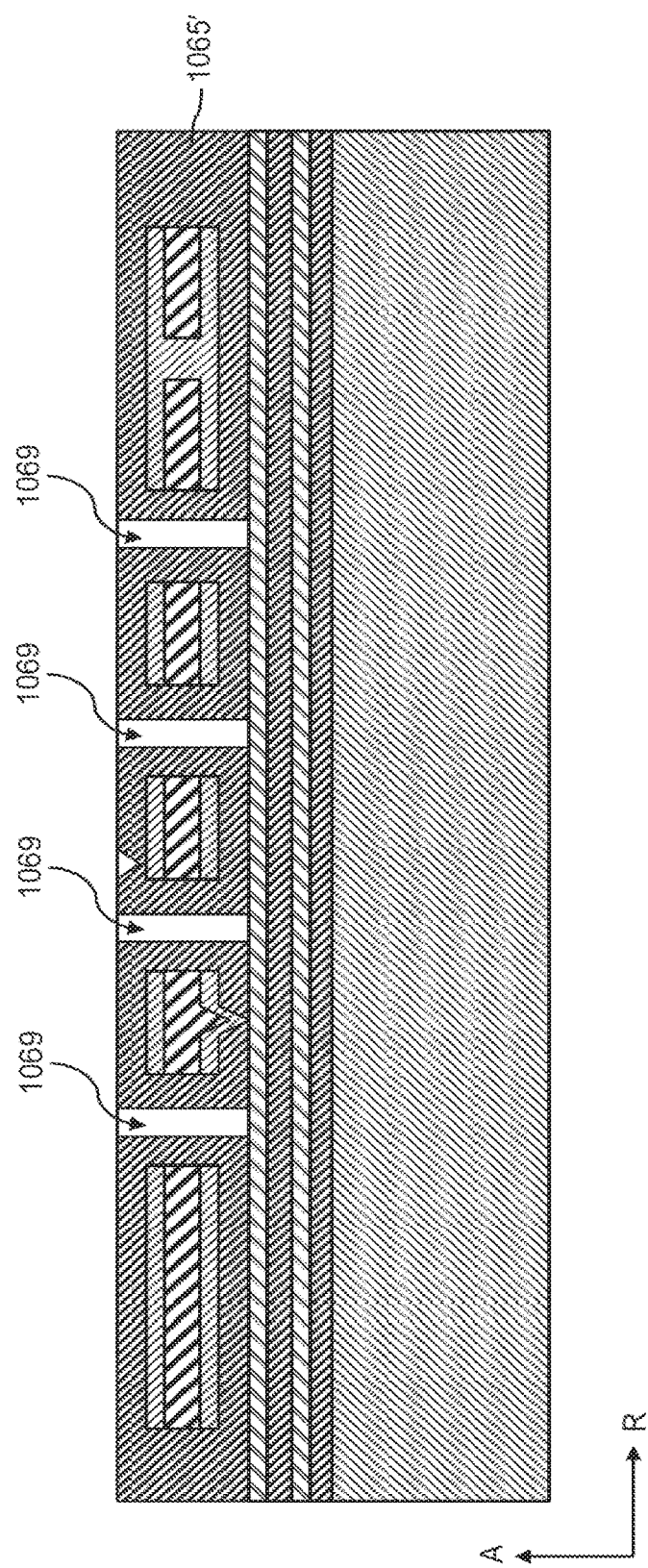

Subsequently, as shown in FIG. 19, a plurality of passage openings 1069 may be formed, for example by etching, for producing a plurality of spacers in the thickness direction of the sacrificial layer 1065'. The passage openings 1069 extend through the radiation element 1030 in order to form spacers that extend through the radiation element 1030. The passage openings 1069 may have a diameter of approximately 1 µm.

Figure 20:
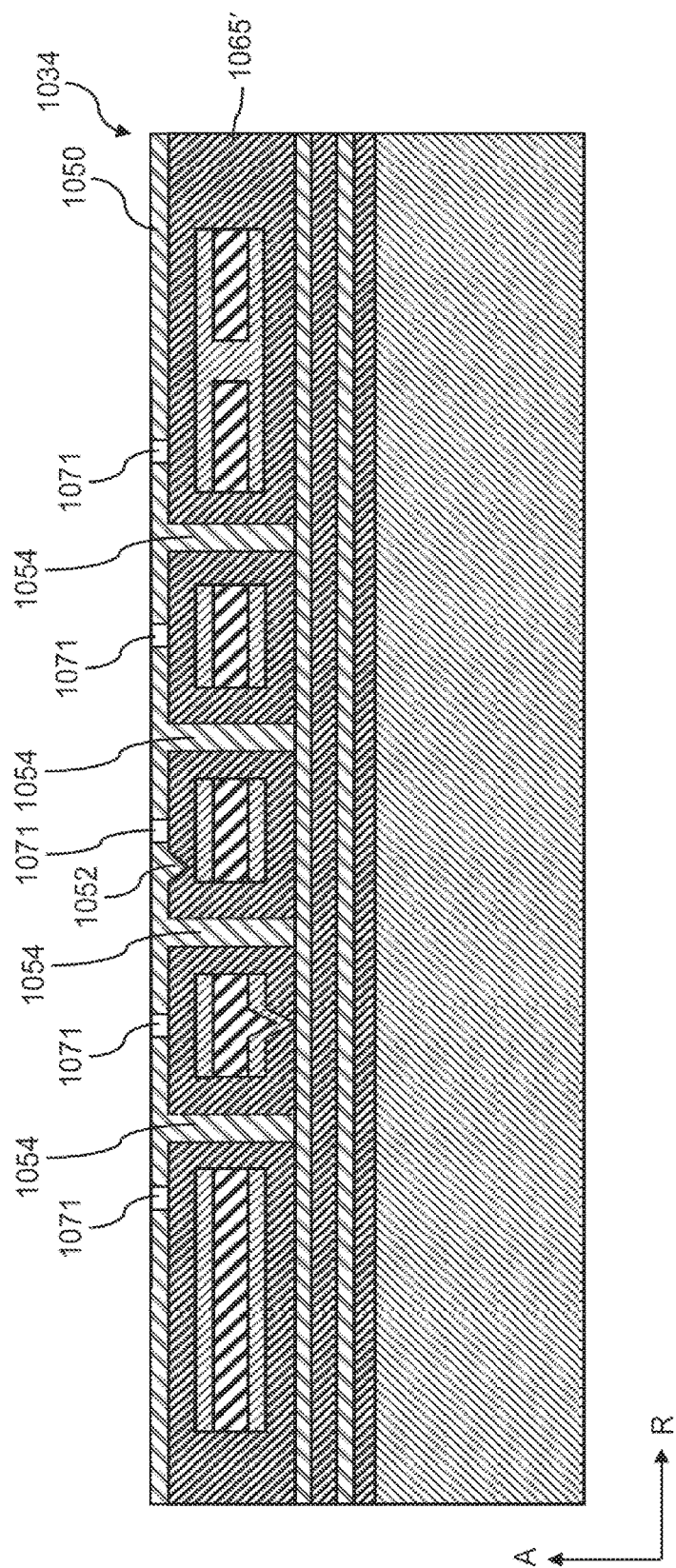

As shown in FIG. 20, a further layer, for instance made of polysilicon, can be formed on the planarized surface of the sacrificial layer 1065' and in the plurality of passage openings 1069 and in the tapering opening 1067, as a result of which a substrate 1050 of a second housing wall 1034 and a plurality of spacers 1054 that are integral with the substrate 1050 are formed. Here, an anti-adhesion protrusion 1052 is likewise integrally formed with the substrate 1050 of the second housing wall 1034 at the same time. The outer surface of the substrate 1050 can be subsequently planarized, for example by chemical-mechanical polishing. Moreover, a plurality of etching openings 1071 can be formed in the substrate 1050. The etching openings 1071 may have a diameter of several 100 nm, for example 200 nm.

Figure 21:
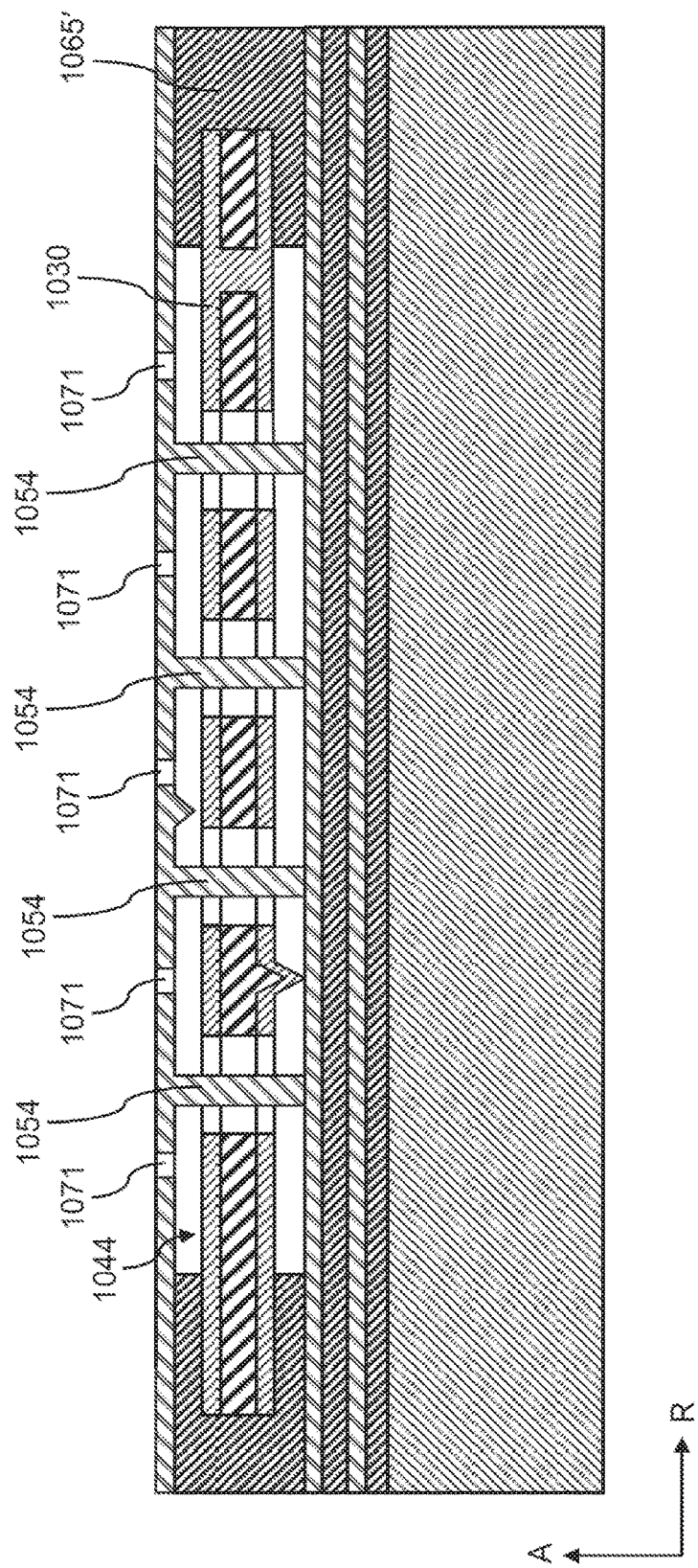

As shown in FIG. 21, the sacrificial layer 1065' can be etched in regions through the etching openings 1071, for instance with hydrofluoric acid, in order, for the purposes of forming a radiation element receptacle chamber 1044, to separate the radiation element 1030 in regions from the first housing wall 1032 and/or from the second housing wall 1034. Moreover, the spacers 1054 can be separated from the radiation element 1030 thereby.

Here it is also possible to leave webs made of sacrificial layer material between the radiation element 1030 and the first housing wall 1032 or second housing wall 1034 in order to form spacers according to the radiation source 804 shown in FIG. 10.

Figure 22:
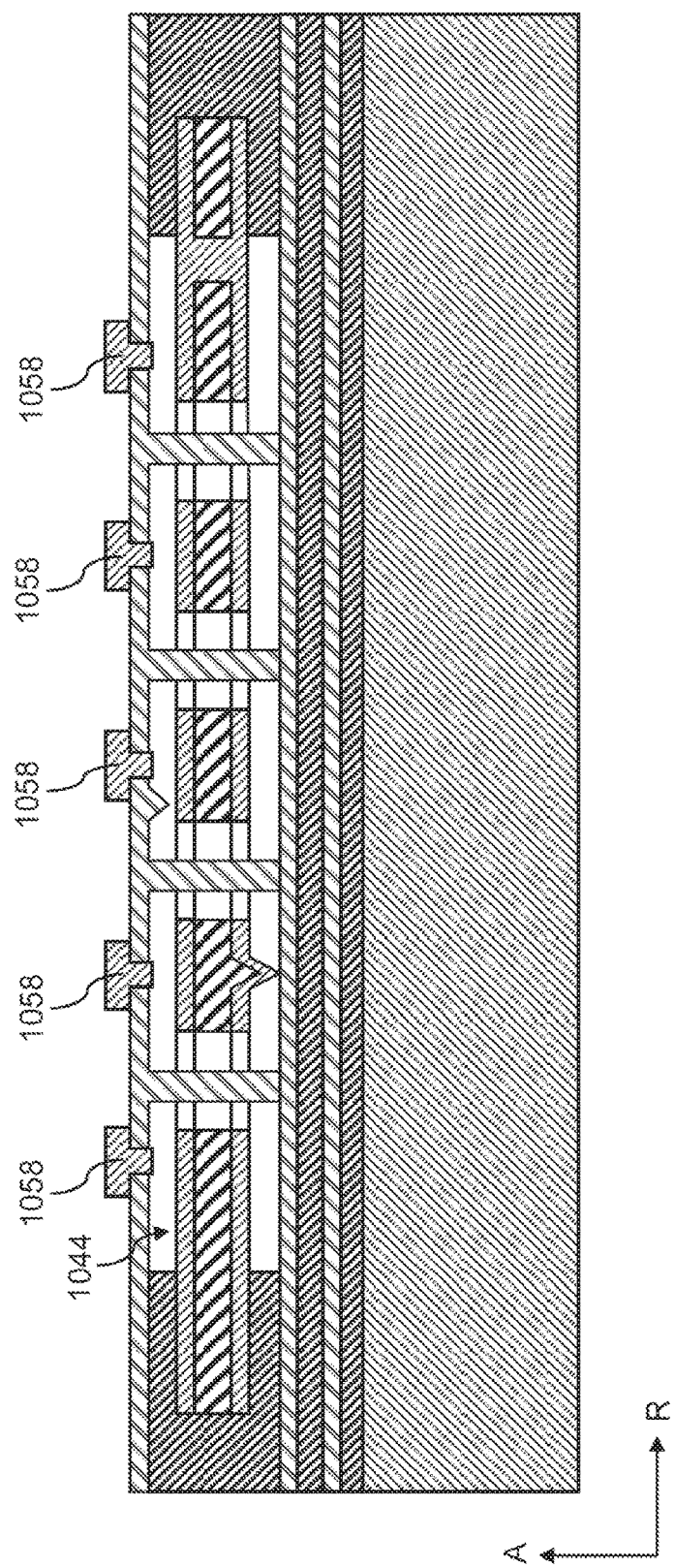

Then, as shown in FIG. 22, the etching openings 1071 can be sealed by sealing elements 1058, for example made of an oxide and/or a nitride. Sealing can be effectuated at a pressure that is lower than normal pressure (1013.25 mbar). Optionally, the pressure may be less than 100 mbar, as a further option less than 50 mbar or even less than 10 mbar.

Figure 23:
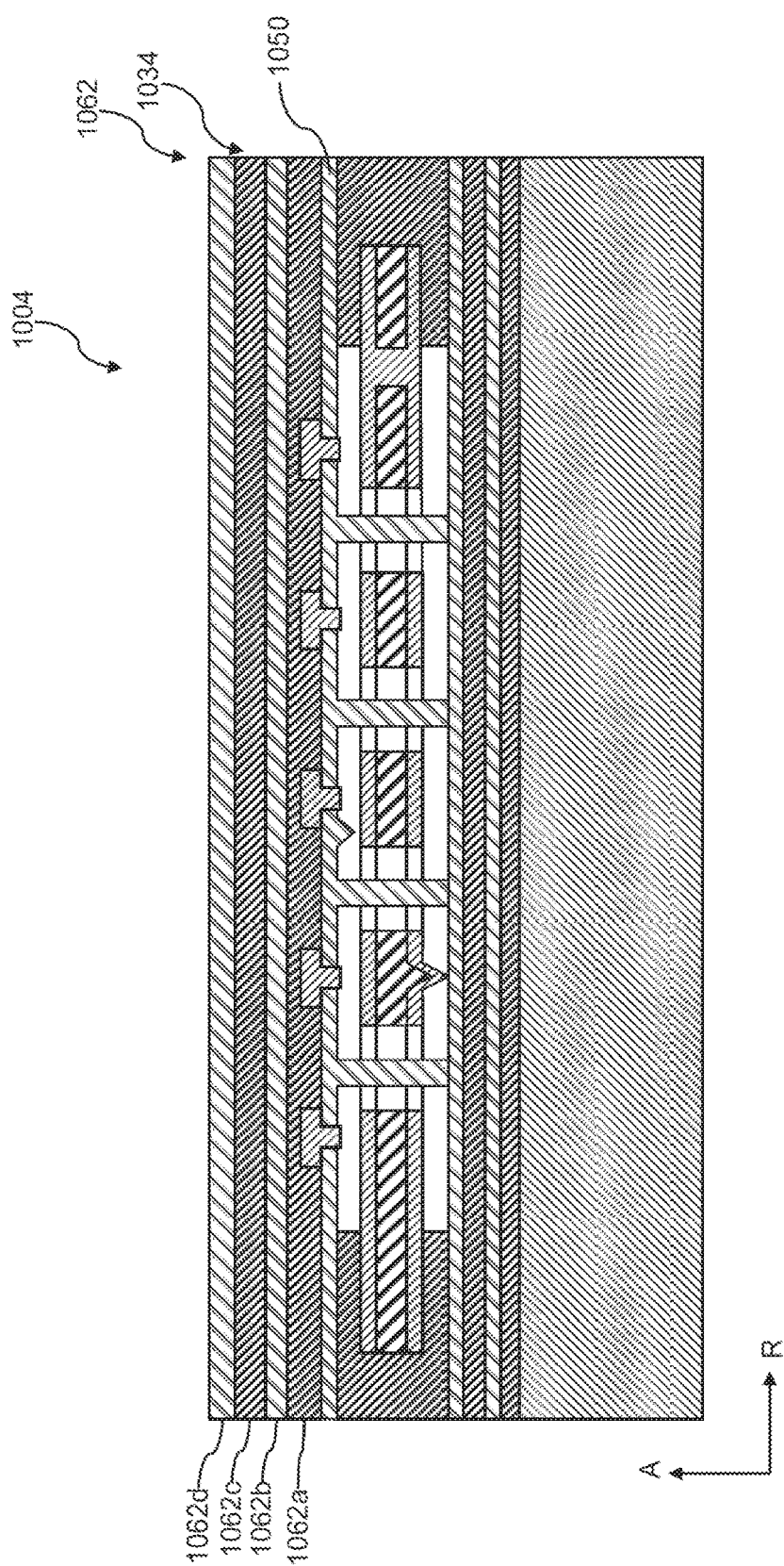

After sealing the etching openings 1071, it is possible, as shown in FIG. 23, to form a filter 1062 on the side of the substrate 1050 facing away from the radiation element receptacle chamber 1044, for example by depositing a plurality of layers 1062a, 1062b, 1062c, 1062d onto the substrate 1050. At least two of the layers 1062a, 1062b, 1062c, 1062d may have refractive indices that differ from one another. The layers 1062a, 1062b, 1062c, 1062d may be formed from $SiO_2$ or polysilicon. Here, the substrate 1050 may also serve as a layer of the filter 1062. As a result of this, the production of the second housing wall 1034, and consequently of the radiation source 1004, is completed.

Moreover, the exemplary method may also include the formation of at least two contacting regions for electrical contacting of the radiation element 1030.

Figure 24:
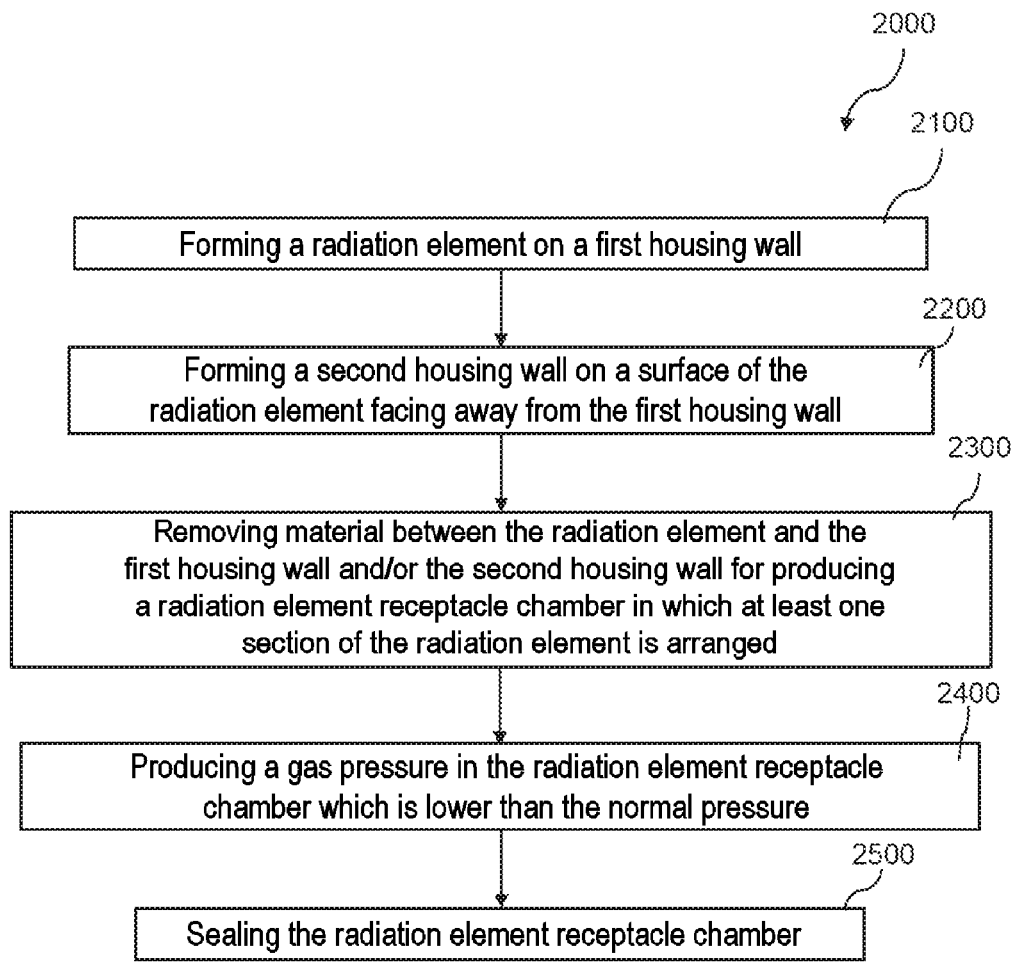
FIG. 24 shows a flowchart of an exemplary method for producing an exemplary radiation source.

FIG. 24 shows a flowchart of an exemplary method 2000 for producing a radiation source. The method 2000 includes: forming a radiation element on a first housing wall (2100), forming a second housing wall on a surface of the radiation element facing away from the first housing wall (2200), removing material between the radiation element and the first housing wall and/or the second housing wall for producing a radiation element receptacle chamber in which at least one section of the radiation element is arranged (2300), producing a gas pressure in the radiation element receptacle chamber which is lower than the normal pressure (2400), and
sealing the radiation element receptacle chamber (2500).

Several examples of the present disclosure will be described below.

Example 1 is a gas analysis apparatus, having: a gas chamber for receiving a gas to be analysed, a radiation source configured to emit electromagnetic radiation into the gas chamber, wherein the electromagnetic radiation is configured to selectively excite molecules of a gas to be analysed, and a sensor configured to detect a physical variable which contains information about a degree of interaction between the electromagnetic radiation emitted by the radiation source and the gas received in the gas chamber, wherein the radiation source has: an electrically heatable planar radiation element configured to emit electromagnetic radiation and a housing with a first and a second planar housing wall which, therebetween, define and immediately delimit a radiation element receptacle chamber that is separated in a fluid-tight manner from the surroundings of the radiation source, in which a lower gas pressure is prevalent in comparison with the normal pressure and in which at least one section of the radiation element is arranged at a distance from the first housing wall and/or the second housing wall, wherein the first housing wall and/or the second housing wall is/are transparent to the electromagnetic radiation that is emittable by the radiation element.

In example 2, the subject matter of example 1 may optionally further include that the gas pressure in the radiation element receptacle chamber is less than 100 mbar, optionally less than 50 mbar, as a further option less than 10 mbar.

In example 3, the subject matter of example 1 or 2 may optionally further include that the radiation source has at least one spacer between the first housing wall and the second housing wall, said spacer being completely arranged in the radiation element receptacle chamber.

In example 4, the subject matter of example 3 may optionally further include that at least one spacer has permanent physical contact with the first housing wall and/or the second housing wall, optionally an integral embodiment with the first housing wall and/or the second housing wall.

In example 5, the subject matter of example 3 or 4 may optionally further include that the radiation element has at least one passage opening extending in its thickness direction, at least one section of a spacer being arranged in said passage opening.

In example 6, the subject matter of example 5 may optionally further include that the spacer is spaced apart from the radiation element, optionally completely spaced apart.

In example 7, the subject matter of any one of examples 3 to 6 may optionally further include that at least one spacer has permanent physical contact with the radiation element, optionally an integral embodiment with the radiation element.

In example 8, the subject matter of any one of examples 1 to 7 may optionally further include that the radiation element has a layer structure with an electrically conductive layer and at least one electrically insulating layer, wherein, optionally, the electrically conductive layer is received in the thickness direction of the radiation element between two electrically insulating layers which are spaced apart from the first housing wall and/or the second housing wall.

In example 9, the subject matter of any one of examples 1 to 8 may optionally further include that the first housing wall and/or the second housing wall has/have a filter or is/are embodied as a filter, said filter being configured to transmit, in a wavelength-selective manner, the electromagnetic radiation that is emittable by the radiation element.

In example 10, the subject matter of example 9 may optionally further include that the filter has a filter with fixedly predetermined transmission properties or the filter is embodied as such and/or that the filter has an adjustable filter or the filter is embodied as an adjustable filter, the transmission properties of said adjustable filter being adjustable.

In example 11, the subject matter of any one of examples 1 to 10 may optionally further include that the first housing wall and/or the second housing wall has/have a reflector or the first housing wall and/or the second housing wall is/are embodied as a reflector, said reflector being configured to reflect the electromagnetic radiation that is emittable by the radiation element.

In example 12, the subject matter of example 11 may optionally further include that the reflector has a reflectance of at least 0.2, optionally of at least 0.5, as a further option of at least 0.8, in the infrared frequency range and/or in the visible frequency range and/or in the ultraviolet frequency range.

In example 13, the subject matter of example 11 or 12 may optionally further include that the reflector has a metallic reflector and/or a Bragg reflector or the reflector is embodied as such.

In example 14, the subject matter of example 9 or 10 and any one of examples 11 to 13 may optionally further include that the first housing wall or the second housing wall has a filter immediately delimiting the radiation element receptacle chamber and the respective other housing wall has a reflector that immediately delimits the radiation element receptacle chamber, wherein the distance between the filter and reflector corresponds to an integer multiple of a half wavelength contained in the transmission range of the filter.

In example 15, the subject matter of any one of examples 1 to 14 may optionally further include that the radiation source is configured to emit electromagnetic radiation with a time-varying intensity into the gas chamber in order to excite molecules of the gas to be analysed in time-varying manner, as a result of which sound waves are produced as a physical variable which contains information about the degree of interaction between the electromagnetic radiation emitted by the radiation source and the gas received in the gas chamber, wherein the sensor has a sound wave sensor or is embodied as such, said soundwave sensor being configured to detect the sound waves produced by the electromagnetic radiation.

In example 16, the subject matter of example 15 may optionally further include that the soundwave sensor is arranged in the gas chamber.

In example 17, the subject matter of example 15 may optionally further include that the soundwave sensor is arranged in a reference gas chamber that is separated from the gas chamber in a fluid-tight manner and filled with a reference gas, wherein the reference gas contains a gas type with a predetermined concentration, the concentration of which in the gas chamber is to be ascertained.

In example 18, the subject matter of any one of examples 1 to 17 may optionally further include that the sensor has a photodetector or is embodied as such, said photodetector being configured to detect electromagnetic radiation emitted by the radiation source.

Example 19 is a method for producing a radiation source of a gas analysis apparatus according to any one of examples 1 to 18, including: forming a radiation element on a first housing wall, forming a second housing wall on a surface of the radiation element facing away from the first housing wall, removing material between the radiation element and the first housing wall and/or between the radiation element and the second housing wall for producing a radiation element receptacle chamber in which at least one section of the radiation element is arranged, producing a gas pressure in the radiation element receptacle chamber which is lower than the normal pressure, and sealing the radiation element receptacle chamber while a gas pressure that is lower than the normal pressure is prevalent in the radiation element receptacle chamber.

In example 20, the subject matter of example 19 may optionally further include that the gas pressure in the radiation element receptacle chamber is lower than 100 mbar, optionally lower than 50 mbar, as a further option lower than 10 mbar.

In example 21, the subject matter of example 19 or 20 may further optionally include that, before forming the radiation element, a sacrificial layer is formed on the first housing wall, the radiation element subsequently being formed on said sacrificial layer, wherein some of the sacrificial layer between the radiation element and the first housing wall is removed for forming the radiation element receptacle chamber.

In example 22, the subject matter of any one of examples 19 to 21 may optionally further include that, before forming the second housing wall, a sacrificial layer is formed on the radiation element, the second housing wall subsequently being formed on said sacrificial layer, wherein some of the sacrificial layer between the radiation element and the second housing wall is removed for forming the radiation element receptacle chamber.

In example 23, the subject matter of any one of examples 19 to 22 may optionally further include that forming the radiation element includes: forming an electrically conductive layer from an electrically conductive material and forming at least one electrically insulating layer from an electrically insulating material, optionally a plurality of electrically insulating layers from electrically insulating materials, wherein the electrically conductive layer is formed, at least in sections, on at least one electrically insulating layer and/or at least one electrically insulating layer is formed, at least in sections, on the electrically conductive layer.

In example 24, the subject matter of example 23 may optionally further include that material between an electrically insulating layer of the radiation element and the first housing wall and/or material between an electrically insulating layer of the radiation element and the second housing wall is removed for forming the radiation element receptacle chamber.

In example 25, the subject matter of any one of examples 19 to 24 may optionally further include: producing the first housing wall, wherein producing the first housing wall may include: forming a filter configured to transmit, in a wavelength selective manner, the electromagnetic radiation that is emittable by the radiation element and/or forming a reflector configured to reflect, optionally in a wavelength-selective manner, the electromagnetic radiation that is emittable by the radiation element.

In example 26, the subject matter of example 25 may optionally further include that forming the filter includes: forming a plurality of layers, wherein at least two of the layers have refractive indices that differ from one another, and/or forming an adjustable filter, the transmission properties of which are adjustable.

In example 27, the subject matter of example 25 or 26 may optionally further include that forming the reflector includes: forming at least one reflective layer, optionally a metallic layer, and/or forming a plurality of layers, wherein at least two of the layers have refractive indices that differ from one another.

In example 28, the subject matter of any one of examples 19 to 27 may optionally further include that forming the second housing wall includes: forming a filter configured to transmit, in a wavelength-selective manner, the electromagnetic radiation that is emittable by the radiation element and/or forming a reflector configured to reflect, optionally in a wavelength-selective manner, the electromagnetic radiation that is emittable by the radiation element.

In example 29, the subject matter of example 28 may optionally further include that forming the filter includes: forming a plurality of layers, wherein at least two of the layers have refractive indices that differ from one another, and/or forming an adjustable filter, the transmission properties of which are adjustable.

In example 30, the subject matter of example 28 or 29 may optionally further include that forming the reflector includes: forming at least one reflective layer, optionally a metallic layer, and/or forming a plurality of layers, wherein at least two of the layers have refractive indices that differ from one another.

In example 31, the subject matter of any one of examples 19 to 30 may optionally further include: forming at least one spacer, optionally a plurality of spacers, between the first housing wall and the second housing wall.

In example 32, the subject matter of example 31 may optionally further include that the at least one spacer is formed when forming the second housing wall and/or when removing material between the radiation element and the first housing wall and/or the second housing wall for producing the radiation element receptacle chamber.

In example 33, the subject matter of any one of examples 19 to 32 may optionally further include: forming at least one passage opening, optionally a plurality of passage openings, in the radiation element, said passage opening or passage openings extending continuously in the thickness direction of the radiation element.

In example 34, the subject matter of example 31 or 32 and of example 33 may optionally further include that at least one spacer is formed in a passage opening formed in the radiation element, wherein, optionally, the at least one spacer is completely separated from the radiation element.

In example 35, the subject matter of any one of examples 19 to 34 may optionally further include: forming, on the radiation element, at least one anti-adhesion protrusion projecting in the direction of the first housing wall or second housing wall and/or forming, on the first housing wall and/or the second housing wall, at least one anti-adhesion protrusion projecting in the direction of the radiation element.

Various embodiments provide a gas analysis apparatus, by means of which the composition of a gas to be analysed is precisely determinable.

According to one aspect of the present disclosure, a gas analysis apparatus is provided, the latter having: a gas chamber for receiving a gas to be analysed, a radiation source configured to emit electromagnetic radiation into the gas chamber, wherein the electromagnetic radiation is configured to selectively excite molecules of a gas to be analysed, and a sensor configured to detect a physical variable which contains information about a degree of interaction between the electromagnetic radiation emitted by the radiation source and the gas received in the gas chamber, wherein the radiation source has: an electrically heatable planar radiation element configured to emit electromagnetic radiation and a housing with a first and a second planar housing wall which, therebetween, define and immediately delimit a radiation element receptacle chamber that is separated in a fluid-tight manner from the surroundings of the radiation source, in which a lower gas pressure is prevalent in comparison with the normal pressure and in which at least one section of the radiation element is arranged at a distance from the first housing wall and/or the second housing wall, wherein the first housing wall and/or the second housing wall is/are transparent to the electromagnetic radiation that is emittable by the radiation element.

According to a further aspect, a method for producing a radiation source of a gas analysis apparatus as described above is provided, including: forming a radiation element on a first housing wall, forming a second housing wall on a surface of the radiation element facing away from the first housing wall, removing material between the radiation element and the first housing wall and/or between the radiation element and the second housing wall for producing a radiation element receptacle chamber in which at least one section of the radiation element is arranged, producing a gas pressure in the radiation element receptacle chamber which is lower than the normal pressure, and sealing the radiation element receptacle chamber.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A gas analysis apparatus, comprising:
a gas chamber for receiving a gas to be analysed,
a radiation source configured to emit electromagnetic radiation into the gas chamber, wherein the electromagnetic radiation is configured to selectively excite molecules of a gas to be analysed, and
a sensor configured to detect a physical variable which contains information about a degree of interaction between the electromagnetic radiation emitted by the radiation source and the gas received in the gas chamber,
wherein the radiation source comprises:
an electrically heatable planar radiation element configured to emit electromagnetic radiation and a housing with a first planar housing wall and a second planar housing wall which, therebetween, define and immediately delimit a radiation element receptacle chamber that is separated in a fluid-tight manner from surroundings of the radiation source, in which a lower gas pressure is prevalent in comparison with the normal pressure and in which at least one section of the radiation element is arranged at a distance from at least one of the first housing wall or the second housing wall,
wherein at least one of the first housing wall or the second housing wall is transparent to the electromagnetic radiation that is emittable by the radiation element.

2. The gas analysis apparatus of claim 1,
wherein the gas pressure in the radiation element receptacle chamber is less than 100 mbar.

3. The gas analysis apparatus of claim 1,
wherein the radiation source has at least one spacer between the first housing wall and the second housing wall, said spacer being completely arranged in the radiation element receptacle chamber.

4. The gas analysis apparatus of claim 3,
wherein at least one spacer has permanent physical contact with the radiation element.

5. The gas analysis apparatus of claim 1,
wherein the radiation element has a layer structure with an electrically conductive layer and at least one electrically insulating layer.

6. The gas analysis apparatus of claim 1,
wherein at least one of the first housing wall or the second housing wall has a filter or is embodied as a filter, said filter being configured to transmit, in a wavelength-selective manner, the electromagnetic radiation that is emittable by the radiation element.

7. The gas analysis apparatus of claim 6, wherein the filter has a filter with fixedly predetermined transmission properties or the filter is embodied as such.

8. The gas analysis apparatus of claim 6, wherein the filter has an adjustable filter or the filter is embodied as an adjustable filter, the transmission properties of said adjustable filter being adjustable.

9. The gas analysis apparatus of claim 6, wherein the first housing wall or the second housing wall has a filter immediately delimiting the radiation element receptacle chamber and the respective other housing wall has a reflector that immediately delimits the radiation element receptacle chamber, wherein the distance between the filter and reflector corresponds to an integer multiple of a half wavelength contained in a transmission range of the filter.

10. The gas analysis apparatus of claim 1, wherein at least one of the first housing wall or the second housing wall has a reflector or at least one of the first housing wall or the second housing wall is embodied as a reflector, said reflector being configured to reflect the electromagnetic radiation that is emittable by the radiation element.

11. The gas analysis apparatus of claim 10, wherein the reflector has at least one of a metallic reflector or a Bragg reflector or the reflector is embodied as such.

12. A method for producing a radiation source of a gas analysis apparatus, the gas analysis apparatus comprising:
a gas chamber for receiving a gas to be analysed,
a radiation source configured to emit electromagnetic radiation into the gas chamber, wherein the electromagnetic radiation is configured to selectively excite molecules of a gas to be analysed, and
a sensor configured to detect a physical variable which contains information about a degree of interaction between the electromagnetic radiation emitted by the radiation source and the gas received in the gas chamber,
wherein the radiation source comprises:
an electrically heatable planar radiation element configured to emit electromagnetic radiation and a housing with a first planar housing wall and a second planar housing wall winch, therebetween, define and immediately delimit a radiation element receptacle chamber that is separated in a fluid-tight manner from surroundings of the radiation source, in which a lower gas pressure is prevalent in comparison with the normal pressure and in which at least one section of the radiation element is arranged at a distance from at least one of the first housing wall or the second housing wall,
wherein at least one of the first housing wall or the second housing wall is transparent to the electromagnetic radiation that is emittable by the radiation element;
the method comprising;
forming a radiation element on a first housing wall,
forming a second housing wall on a surface of the radiation element facing away from the first housing wall,
removing material at least one of between the radiation element and the first housing wall between the radiation element and the second housing wall for producing a radiation element receptacle chamber in which at least one section of the radiation element is arranged,
producing a gas pressure in the radiation element receptacle chamber which is lower than the normal pressure, and
sealing the radiation element receptacle chamber.

13. The method of claim 12, wherein, before forming the radiation element, a sacrificial layer is formed on the first housing wall, the radiation element subsequently being formed on said sacrificial layer, wherein some of the sacrificial layer between the radiation element and the first housing wall is removed for forming the radiation element receptacle chamber.

14. The method of claim 12, wherein, before forming the second housing wall, a sacrificial layer is formed on the radiation element, the second housing wall subsequently being formed on said sacrificial layer, wherein some of the sacrificial layer between the radiation element and the second housing wall is removed for forming the radiation element receptacle chamber.

15. The method of claim 12, wherein forming the radiation element comprises:
forming an electrically conductive layer from an electrically conductive material, and
forming at least one electrically insulating layer from an electrically insulating material,
wherein at least one of the electrically conductive layer is formed, at least in sections, on at least one of at least one electrically insulating layer or at least one electrically insulating layer is formed, at least in sections, on the electrically conductive layer.

16. The method of claim 12, further comprising:
producing the first housing wall, wherein producing the first housing wall comprises:
at least one of forming a filter configured to transmit, in a wavelength selective manner, the electromagnetic radiation that is emittable by the radiation element or forming a reflector configured to reflect the electromagnetic radiation that is emittable by the radiation element.

17. The method of claim 16, wherein forming the reflector comprises: at least one of forming at least one reflective layer or forming a plurality of layers, wherein at least two of the layers have refractive indices that differ from one another.

18. The method of claim 12, wherein forming the second housing wall comprises:
at least one of forming a filter configured to transmit, in a wavelength-selective manner, the electromagnetic radiation that is emittable by the radiation element or forming a reflector configured to reflect the electromagnetic radiation that is emittable by the radiation element.

19. The method of claim 18, wherein forming the filter comprises: at least one of forming a plurality of layers, wherein at least two of the layers have refractive indices that differ from one another, or forming an adjustable filter, transmission properties of which are adjustable.

20. The method of claim 18, wherein forming the reflector comprises: at least one of forming at least one reflective layer or forming a plurality of layers, wherein at least two of the layers have refractive indices that differ from one another.

21. The method of claim 12, further comprising:
forming at least one spacer between the first housing wall and the second housing wall.

22. The method of claim 21,
wherein the at least one spacer is formed at least one of when forming the second housing wall or when removing material between the radiation element and the first housing wall or the second housing wall for producing the radiation element receptacle chamber.

23. The method of claim 21,
wherein at least one spacer is formed in a passage opening formed in the radiation element.

24. The method of claim 12, further comprising:
forming at least one passage opening in the radiation element, said passage opening or passage openings extending continuously in a thickness direction of the radiation element.

25. The method of claim 12, further comprising:
at least one of forming, on the radiation element, at least one anti-adhesion protrusion projecting in the direction of the first housing wall or second housing wall or forming, on at least one of the first housing wall or the second housing wall, at least one anti-adhesion protrusion projecting in the direction of the radiation element.

26. A gas analysis apparatus, comprising:
a gas chamber for receiving a gas to be analysed,
a radiation source configured to emit electromagnetic radiation into the gas chamber, wherein the electromagnetic radiation is configured to selectively excite molecules of a gas to be analysed, and
a sensor configured to detect a physical variable which contains information about a degree of interaction between the electromagnetic radiation emitted by the radiation source and the gas received in the gas chamber,
wherein the radiation source comprises:
an electrically heatable planar radiation element configured to emit electromagnetic radiation and a housing with a first planar housing wall and a second planar housing wall which, therebetween, define and immediately delimit a radiation element receptacle chamber that is separated in a fluid-tight manner from surroundings of the radiation source, in which a lower gas pressure is prevalent in comparison with the normal pressure and in which at least one section of the radiation element is arranged at a distance from at least one of the first housing wall or the second housing wall,
wherein at least one of the first housing wall or the second housing wall is transparent to the electromagnetic radiation that is emittable by the radiation element,
wherein the radiation source has at least one spacer between the first housing wall and the second housing wall, said spacer being completely arranged in the radiation element receptacle chamber, and
wherein the radiation element has at least one passage opening extending in its thickness direction, at least one section of a spacer being arranged in said passage opening.

* * * * *